United States Patent
Shakibi Gilani

(10) Patent No.: US 9,474,460 B2
(45) Date of Patent: Oct. 25, 2016

(54) NON-INVASIVE EVALUATION OF CARDIAC REPOLARISATION INSTABILITY FOR RISK STRATIFICATION OF SUDDEN CARDIAC DEATH

(71) Applicant: Jami Shakibi Gilani, Nashville, TN (US)

(72) Inventor: Jami Shakibi Gilani, Nashville, TN (US)

( * ) Notice: Subject to any disclaimer, the term of this patent is extended or adjusted under 35 U.S.C. 154(b) by 0 days.

(21) Appl. No.: 14/338,478

(22) Filed: Jul. 23, 2014

(65) Prior Publication Data

US 2015/0265175 A1   Sep. 24, 2015

Related U.S. Application Data

(63) Continuation of application No. 14/290,014, filed on May 29, 2014, now abandoned.

(60) Provisional application No. 61/954,729, filed on Mar. 18, 2014.

(51) Int. Cl.
| | |
|---|---|
| *A61B 5/0456* | (2006.01) |
| *A61B 5/0472* | (2006.01) |
| *A61B 5/00* | (2006.01) |
| *A61B 5/024* | (2006.01) |
| *A61B 5/04* | (2006.01) |

(52) U.S. Cl.
CPC ......... *A61B 5/0472* (2013.01); *A61B 5/02405* (2013.01); *A61B 5/04017* (2013.01); *A61B 5/0456* (2013.01); *A61B 5/726* (2013.01); *A61B 5/7275* (2013.01)

(58) Field of Classification Search
None
See application file for complete search history.

(56) References Cited

U.S. PATENT DOCUMENTS

| | | | | |
|---|---|---|---|---|
| 3,215,136 | A * | 11/1965 | Glasscock et al. | 600/515 |
| 4,552,156 | A * | 11/1985 | Jackson | 600/516 |
| 7,272,435 | B2 * | 9/2007 | Rowlandson | 600/513 |
| 8,433,395 | B1 * | 4/2013 | Brockway et al. | 600/509 |
| 2002/0188211 | A1 * | 12/2002 | Voith | A61B 5/0205 600/509 |
| 2005/0228626 | A1 * | 10/2005 | Simelius | 703/11 |
| 2006/0189876 | A1 * | 8/2006 | Couderc et al. | 600/516 |
| 2007/0244402 | A1 * | 10/2007 | Brockway et al. | 600/509 |
| 2008/0082132 | A1 * | 4/2008 | Annest et al. | 607/4 |
| 2008/0132799 | A1 * | 6/2008 | Xue | 600/509 |

(Continued)

OTHER PUBLICATIONS

Engel, G., Electrocardiographic Arrhythmia Risk Testing, *Current Problems in Cardiology*, 2004; 29:357-432.

(Continued)

*Primary Examiner* — Erica Lee
(74) *Attorney, Agent, or Firm* — Nicholas Trenkle; Stites & Harbison, PLLC

(57) ABSTRACT

A method for predicting risk of sudden cardiac death through analysis of surface electrocardiographic data includes processing a continuous EKG signal received for a subject over a predetermined time period to identify and extract a plurality of cardiac repolarization phase curves from the EKG signal, assigning each of the cardiac repolarization phase curves into one of a plurality of groups based on a length of the cardiac repolarization phase curve, generating a respective graphical representation for each of the groups in which the cardiac repolarization phase curves assigned to the group are superimposed with one another in the respective graphical representation for the group, and evaluating the graphical representations to assess a risk of sudden cardiac death for the subject based on a classification of cardiac repolarization instability indicated by the graphical representations.

27 Claims, 10 Drawing Sheets

(56) References Cited

U.S. PATENT DOCUMENTS

| | | | |
|---|---|---|---|
| 2009/0137916 A1* | 5/2009 | Maison-Blanche et al. | 600/516 |
| 2013/0096449 A1* | 4/2013 | Patel et al. | 600/516 |
| 2014/0081163 A1* | 3/2014 | Shani et al. | 600/516 |

OTHER PUBLICATIONS

Exner, DV et al., Non-invasive risk assessment early after a myocardial infarction, JACC, 2007, 50:2275-84.

Jouven, X., et al., Predicting Sudden Death in the Population, Circulation, 1999, 99:1978-1983.

Goldberger, JJ et al., American Heart Association: Scientific Statement on Noninvasive risk Stratification techniques for Identifying Patients at Risk for Sudden Cardiac Death, JACC, 2008, 52, 1179-99.

Noseworthy, PA, Newton-Cheh, C., Contemporary reviews in Cardiovascular Medicine—Genetic Determinations of Sudden Cardiac Death, Circulation, 2008, 118: 1854-1863.

Mullner, M. et al, Creatine kinase-mb fraction and cardiac troponin T to diagnose acute myocardial infarction after cardiopulmonary resuscitation, JACC, 1996, 28:1220-1225.

Hondeghem, LM et al, Instability and Triangulation of the Action Potential to Predict Serious Proarrhythmia, Circulation, 2001, 103:2004-13.

Smith JM, Clancy EA, Valeri CR, Ruskin JN, Cohen RJ, Electrical alternans and cardiac electrical instability, Circulation 1988, 77:110-21.

Qi Gao, George, Computerised Detection and Classification of Five Cardiac Conditions, Thesis submitted at Auckland University of Technology, 2003.

Kaur, M., Singh, B & Seema, Comparisons of Different Approaches for removal of Baseline Wander from ECG Signal, 2nd International Conference and Workshop on Emerging Trends in Technology, Proceedings of International Journal of Computer Applications, 2011, 1290-1294.

Zheng Z.J., Croft J.B., Giles W.H., Mensah G.A., Sudden cardiac death in the United States, 1989 to 1998, Circulation. 2001, 104::2158-2163.

Hua W, Zhang LF, Wu YF, et al., Incidence of sudden cardiac death in China: analysis of 4 regional populations, JACC, 2009, 54:1110-1118.

Furutani, M, Trudeau, MC, Hagiwara, N et al., Novel mechanism associated with an inherited cardiac arrhythmia: defective protein trafficking by the mutant HERG (G601S) potassium channel, Circulation, 1999, 99:2290-2294.

Zipes D.P. et al., ACC/AHA/ESC 2006 guidelines for management of patients with ventricular arrhythmias and the prevention of sudden cardiac death, JACC, 2006, 48:e247-e346.

Barron H., T-wave alternans and serious ventricular arrhythmias: a tale of two T-waves*, JACC, 2000, 36(7):2254-2256.

Myerburg RJ, Reddy V, Castellanos A., Indications for Implantable Cardioverter-Defibrillators Based on Evidence and Judgment, JACC, 2009, 54(9):747-763.

Goldberger JJ, Passman R., Implantable Cardioverter-Defibrillator Therapy After Acute Myocardial Infarction: The Results Are Not Shocking, JACC, 2009, 54(22):2001-2005.

Ascione R, Reeves BC, Santo K, Khan N, Angelini GD., Predictors of new malignant ventricular arrhythmias after coronary surgery: A case-control study, JACC, 2004, 43(9):1630-1638.

Maron BJ, Doerer JJ, Haas TS, Tierney DM, Mueller FO., Sudden deaths in young competitive athletes: analysis of 1866 deaths in the United States, 1980-2006, Circulation, 2009, 119:1085-109.

Doevendans PA., Hypertrophic cardiomyopathy: do we have the algorithm for life and death?, Circulation, 2000, 101:1224-1226.

Moss AJ., QTc Prolongation and Sudden Cardiac Death: The Association Is in the Detail, JACC, 2006, 47(2):368-369.

Shakibi Jami G., A Composite Noninvasive Method for Sudden Cardiac Death Risk Stratification, European Society of Cardiology Congress, 2010, 1-13.

Grossman A, et al., Decomposition of Hardy Functions into Square Integrable Wavelets of Constant Shape, Siam J. Math Anal., vol. 15, No. 4 (Jul. 1984), 723-736.

Nelson, Steven D., et al., Clinical Characteristics of Sudden Death Victims in Heritable (Chromosome 1p1-1q1) Conduction and Myocardial Disease, JACC, vol. 32, No. 6, (Nov. 15, 1998) 1717-1723.

Ikeda, T., et al., Combined Assessment of T-Wave Alterans and late Potentials Used to Predict Arrhythmic Events After Myocardial Infarction, Journal of the American College of Cardiology, vol. 35, No. 3 (2000) 722-730.

Edelman, E R, On Causes: Hippocrates, Aristotle, Robert Koch, and the Dread Pirate Roberts, Circulation, 2001, 104:2509-2512.

Gomes, Anthony J., et al., Prediction of Long-term Outcomes by Signal-Averaged Electrocardiography in Patients With Unsustained ventricular Tachycardia, Coronary Artery Disease, and Left Ventricular Dysfunction, Circulation, 2001, 104:436-441.

Mikkelsson, Jussi MD., et al., Glycoprotein IIIa P1 $^{A1/A2}$ Polymorphism and Sudden Death Cardiac Death, Journal of the American College of Cardiology, vol. 36, No. 4 (2000) 722-730.

Taylor, Allen J. et al., A Comparison of the Framingham Risk Index, Coronary Artery Calcification, and Culprit Plaque Morphology in Sudden Cardiac Death, Circulation, 2000, 101:1243-1248.

Makikallio, Timo H., et al., Prediction of Sudden Cardiac Death by Fractal Analysis of Heart Rate Variability in Elderly Subjects, Journal of the American College of Cardiology, vol. 37, No. 5 (2001) 1395-1402.

Haigney, Mark C., et al., QT Interval variability and Spontaneous Ventricular Tachycardiaor Fibrillation in the Multicenter Automatic Defibrillator Implantation Trial (MADIT) II Patients, Journal of the American College of Cardiology, vol. 44, No. 7 (2004) 1481-1487.

Magari, Shannon R. et al., Association of Heart Rate Variability with Occupational and Environmental Exposure to Particulate Air Pollution, Circulation, 2001, 104:986-991.

Grimm, Wolfram, et al., Noninvasive Arrhythmia Risk Stratification Idiopathic Dilated Cadiomyopathy Results of the Marburg Cardiomyopathy Study, Circulation, 2003, 108:2883-2891.

Spooner, Peter M. et al., Sudden Cardiac Death, Genes, and Arrythmogenesis: Consiseration of New Population and Mechanistic Approaches From a National Heart, Lung, and Blood Institute Workshop, Part II, Circulation, 2001, 103:2447-2452.

Spooner, Peter M. et al., Sudden Death, Predictors: An Inflammatory Association, Circulation, 2002, 105:2574-2576.

Tan, Hanno L. et al., Sudden Unexplained Death: Hereditability and Diagnostic Yield of Cardiology and Genetic Examination in Surviving Relatives, Circulation, 2005, 112: 207-213.

Corrado, Domenico, et al., Pre-Participation Screening of Young Competitive Athletes for Prevention of Sudden Cardiac Death, J. Am. Coll. Cardiol., 2008: 52 1981-1989.

Pedretti, Roberto F.E., et al., Cost-Effectiveness Analysis of Invasive and Noninvasive Tests in High Risk Patients Treated With Amiodarone After Acute Myocardial Infaction, JACC, 1998, 31(7): 1481-1489.

Tung, Roderick, et al. A Critical Appraisal of Implantable Cardioverter-Defribillator Therapy for the Prevention of Sudden Cardiac Death, Journal of the American College of Cardiology, vol. 52, No. 14 (2008) 1111-1121.

Morrow, David A, et al., C-Reactive Protein is a Potent Predictor of Mortality Independently of and in Combination with Troponin T in Acute Coronary Syndromes: A TIMI 11A Substudy, JACC, 1998, 31(7): 1460-1465.

Haissaguerre, Michel, et al., Sudden Cardiac Arrest Associated with Early Repolarization, The New England Journal of Medicine, 358:19 (May 8, 2008) 2016-2023.

* cited by examiner

Figure 6A: 59-yr-old male with VT, and structurally normal heart
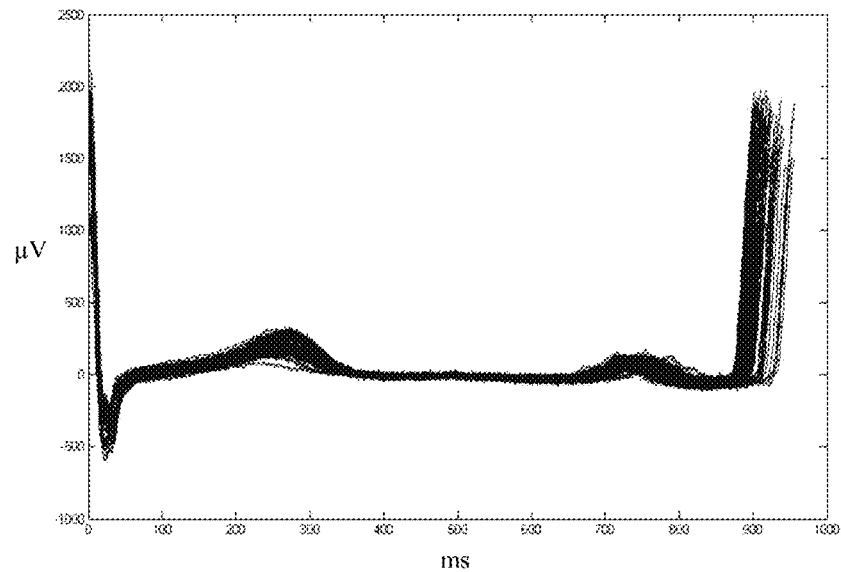
Figure 6B: 59-yr-old male with VT, and structurally normal heart
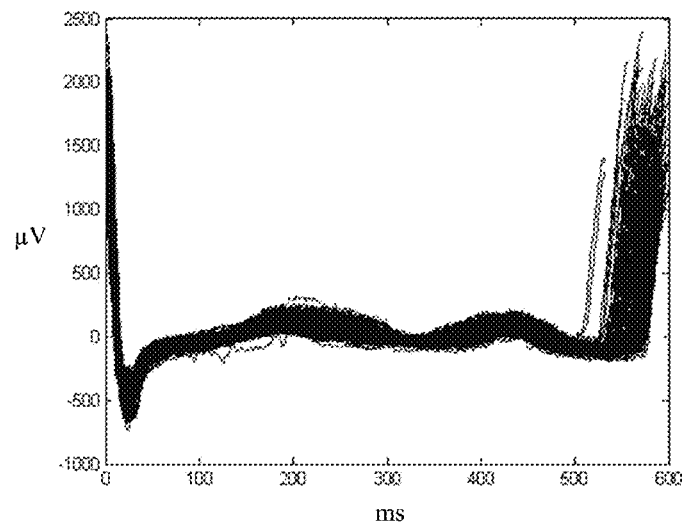

Figure 6C: 12-yr-old male with catechoaminergic VT
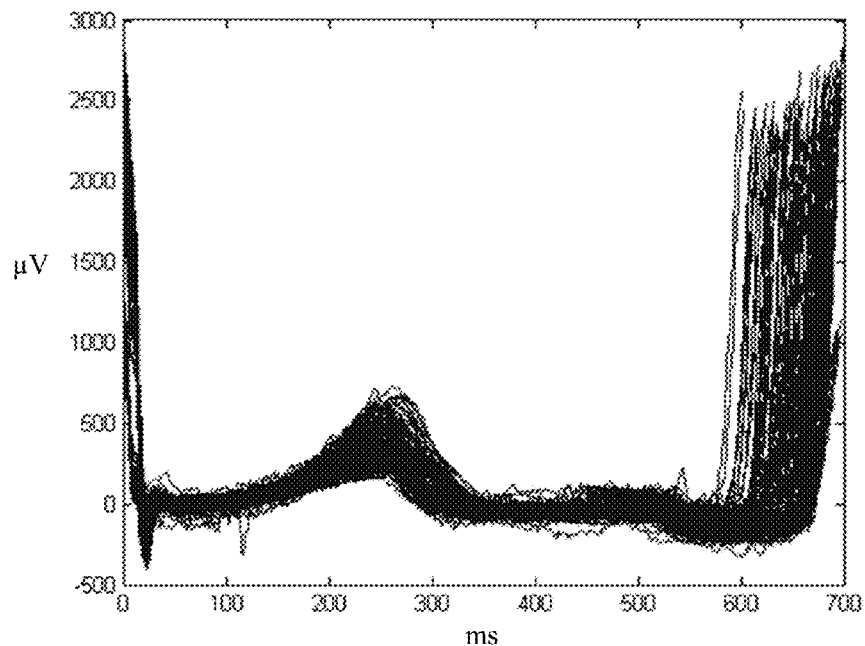
Figure 6D: 12-yr-old male with catechoaminergic VT
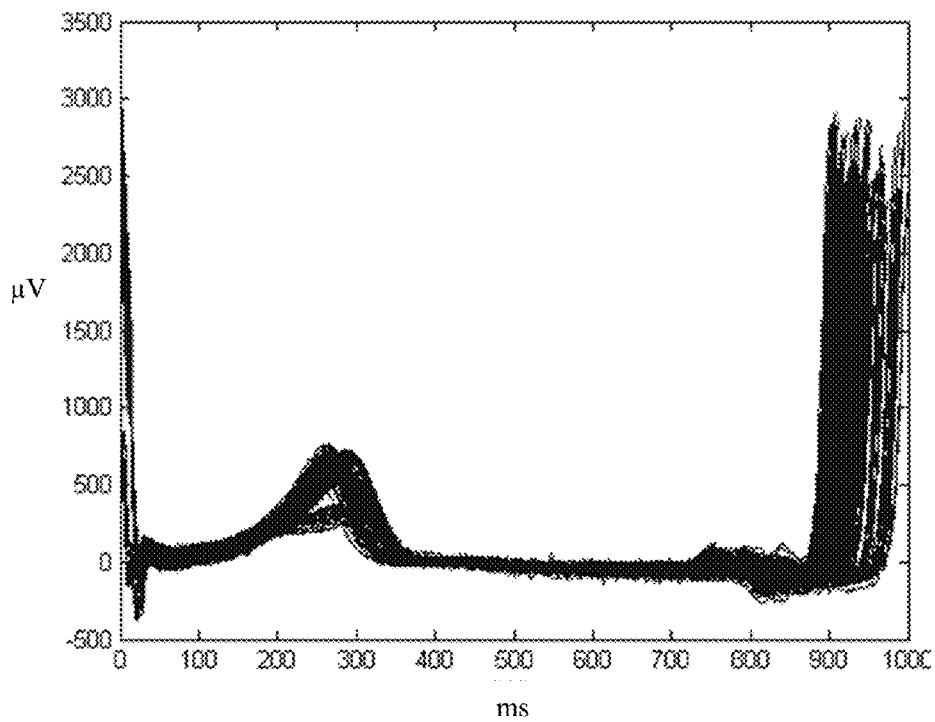

Figure 6E: 56-yr-old with Ischemic Heart Disease
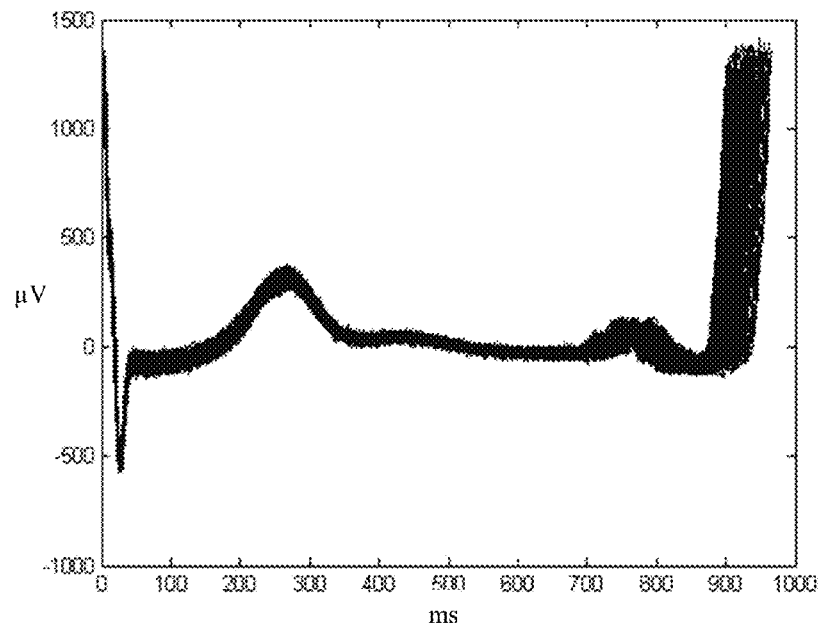
Figure 6F: 14-yr-old Male with Familial Hypertrophic Cardiomyopathy
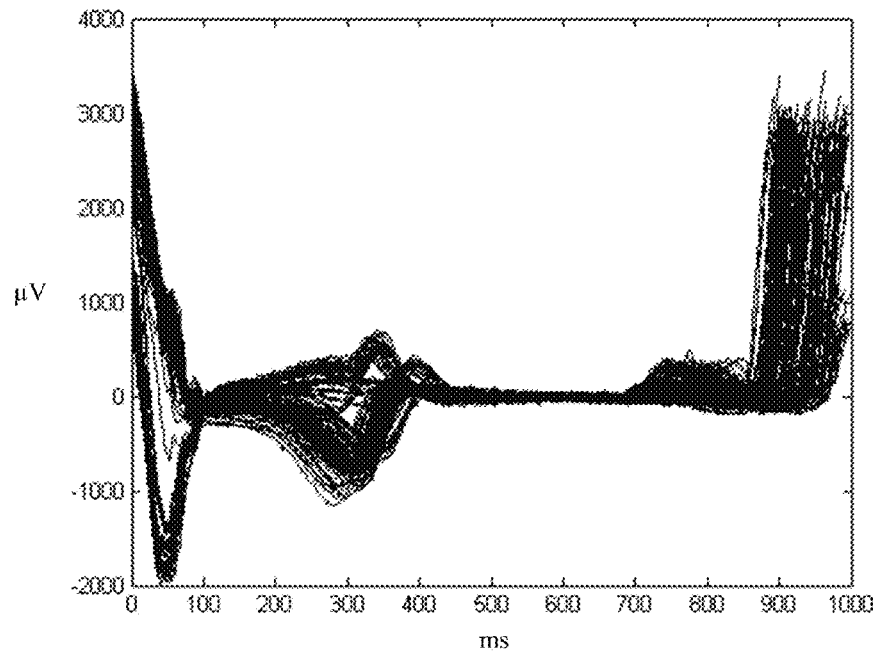

NON-INVASIVE EVALUATION OF CARDIAC REPOLARISATION INSTABILITY FOR RISK STRATIFICATION OF SUDDEN CARDIAC DEATH

CROSS REFERENCE TO RELATED APPLICATIONS

This application is a Continuation of U.S. application Ser. No. 14/290,014, filed May 29, 2014, which claims the benefit of U.S. Provisional Patent Application Ser. No. 61/954,729, filed Mar. 18, 2014, the contents of which are incorporated herein by reference thereto.

BACKGROUND OF THE INVENTION

Exemplary embodiments of the present invention relate to predicting and classifying the risk of sudden cardiac death for medical patients as well as individuals not exhibiting any health conditions. More specifically, exemplary embodiments relate to detection and analysis of cardiac action potential repolarization phase instability as an indicator for predicting risk of sudden cardiac death for subjects through analysis and classification of cardiac repolarization curves extracted from surface electrocardiogram data recorded for the subjects.

Sudden Cardiac Death (SCD) refers to a natural, rapid, and unexpected death from cardiac causes and is the most common lethal manifestation of heart disease. SCD, which is signaled by abrupt loss of consciousness within one hour of the onset of acute symptoms, claims around 17 million lives every year worldwide and between 500 and 1000 lives per day in the US alone. This constitutes approximately 30 percent of the entire global mortality per annum. Despite major advances in the prevention and treatment of cardiac disease, around 60 percent of cardiac deaths are sudden in nature, and the survival rate from SCD currently stands at 1 percent globally and at 5 percent in the US (see Mehra, R., Global Public Health Problem of Sudden Cardiac Death, *Journal of Electrocardiology*, November-December 2007, 40, (Suppl. 6) S118-22; Sovari, A. A., Sudden Cardiac Death, retrieved from emedicine.medscape.com, 2009).

The majority of cases of SCD are due to occurrences of ventricular tachycardia (VT) and ventricular fibrillation (VF). VT and VF are responsible for around 6 million deaths per year around the world (see Mehra, R., Global Public Health Problem of Sudden Cardiac Death, *Journal of Electrocardiology*, November-December 2007, 40, (Suppl. 6) S118-22; Zipes, D. P. Epidemiology and mechanisms of sudden Cardiac Death, *Can. J. Cardiol*, 2005, 21(A): 37A-40A; Wei Hua, et. al., Incidence of Sudden Cardiac Death in China, *JACC*, 2009, 54, 1110-8). The most efficient method currently in use for preventing deaths resulting from VF and VT is by using an implanted cardioverter-defibrillator device (ICD), which is a small battery-powered electrical impulse generating device that is implanted in patients who are at risk of sudden cardiac death due to VT and VF. An ICD operates to detect cardiac arrhythmia and correct it by delivering a brief electrical impulse or shock to the heart.

Nevertheless, accurately and dependably predicting risk of SCD due to VT and VF has been difficult to achieve. Methods for detection of VT and VF should be easy to perform, easily available, non-invasive, highly accurate, and cost-effective (see Engel, G., Electrocardiographic Arrhythmia Risk Testing, *Current Problems in Cardiology*, 2004; 29:357-432; Exner, D. V. et al, Non-invasive risk assessment early after a myocardial infarction, *JACC*, 2007, 50:2275-84). Current methods for such detection, however, fall short of these standards. For example, applications involving invasive electrophysiological study (EPS) that have been practiced have now become outdated as a predictive procedure for SCD, and current criteria for ICD implantation such as ejection fraction (EF) of less than 30 percent, the New York Heart Association (NYHA) functional classes III and IV, and QRS duration of more than 120 milliseconds are likewise viewed as being far from ideal (see Sovari; Jouven, X., et al., Predicting Sudden Death in the Population, *Circulation*, 1999, 99:1978-1983; Goldberger, J. J. et al, American Heart Association: Scientific Statement on Non-invasive risk Stratification techniques for Identifying Patients at Risk for Sudden Cardiac Death, *JACC*, 2008, 52, 1179-99; Riley, L., Risk Stratification for Sudden Death, *Today in Cardiology*, 2007, 10:24; Noseworthy, P. A., Newton-Cheh, C., Contemporary reviews in Cardiovascular Medicine—Genetic Determinations of Sudden Cardiac Death, *Circulation*, 2008, 118: 1854-1863; Schwacke, H. et al, Is there any clinical importance of a non-diagnostic baroreflex sensitivity measurement, *JACC*, 1999, 31(suppl): 1086; Mullner, M. et al, Creatine kinase-mb fraction and cardiac troponin T to diagnose acute myocardial infarction after cardiopulmonary resuscitation, *JACC*, 1996, 28:1220-1225).

SUMMARY OF THE INVENTION

Exemplary embodiments of the present invention are related to a method for predicting risk of sudden cardiac death for a subject through analysis of surface electrocardiographic data recorded for the subject. The method includes processing a continuous surface electrocardiogram (EKG) signal received for the subject over a predetermined period of time to identify and extract a plurality of cardiac repolarization phase curves from the EKG signal, assigning each of the extracted cardiac repolarization phase curves into one of a plurality of groups based on a length of the cardiac repolarization phase curve, generating a respective graphical representation for each of the plurality of groups in which the cardiac repolarization phase curves assigned to the group are superimposed with one another in the respective graphical representation for the group, and evaluating the graphical representations generated for the plurality of groups to assess a risk of sudden cardiac death for the subject based on a classification of cardiac repolarization instability indicated by the graphical representations.

Exemplary embodiments of the present invention that are related to data processing systems and computer program products corresponding to the above-summarized method are also described and claimed herein.

The above-described and other features and advantages realized through the techniques of the present disclosure will be better appreciated and understood with reference to the following detailed description, drawings, and appended claims. Additional features and advantages are realized through the techniques of the present invention. Other embodiments and aspects of the invention are described in detail herein and are considered a part of the claimed invention.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description of exemplary embodiments of the present invention taken in conjunction with the accompanying drawings in which:

FIGS. 6A-6F are illustrations of several examples of graphs of superimposed repolarization curves generated for various subjects in accordance with an exemplary embodiment of the present invention;

Figure 1:
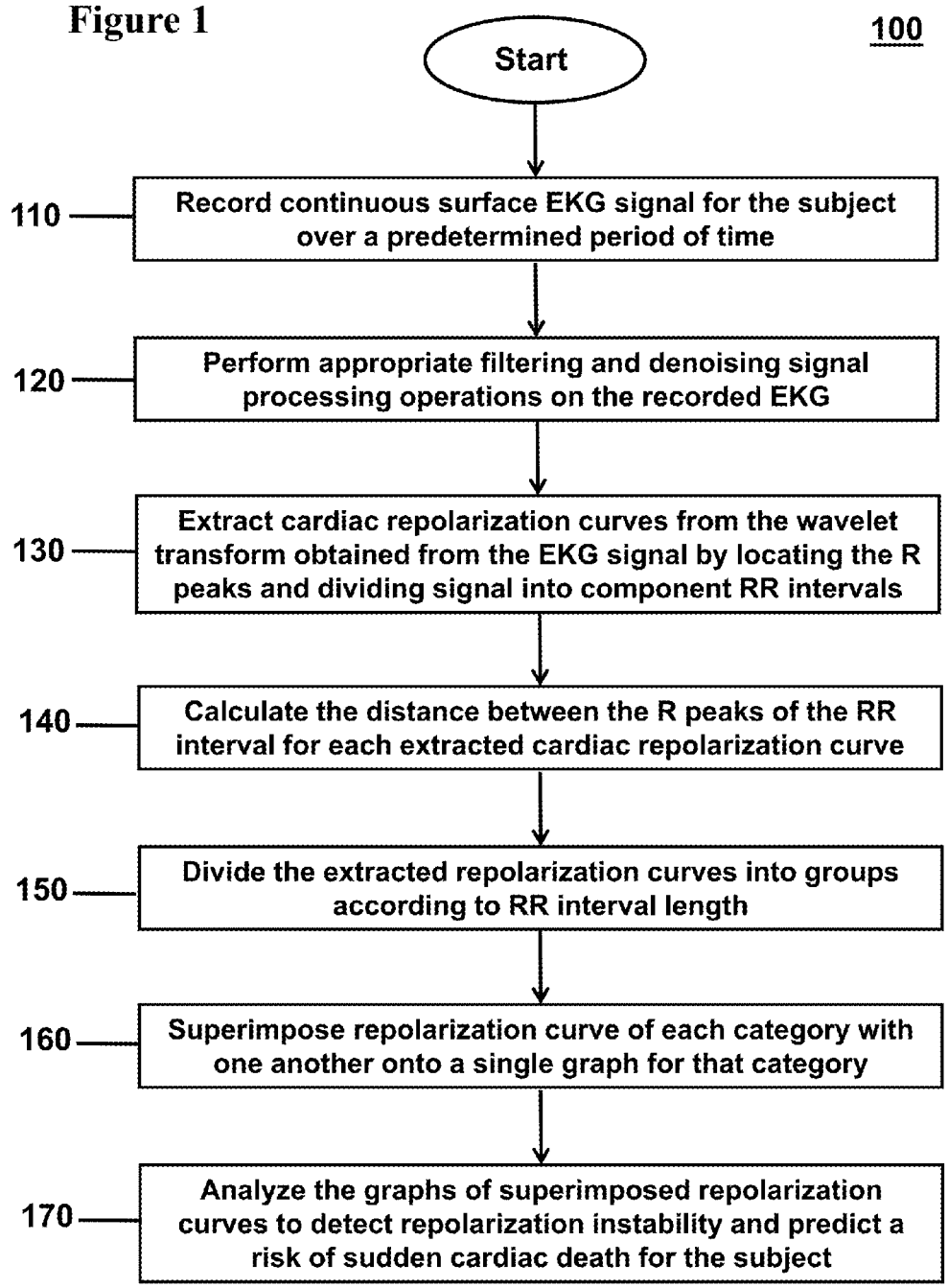
FIG. 1 is a flow diagram illustrating a process of evaluating a risk of sudden cardiac death for a subject through analysis of electrocardiographic data in accordance with an exemplary embodiment of the present invention.

The detailed description explains exemplary embodiments of the present invention, together with advantages and features, by way of example with reference to the drawings, in which similar numbers refer to similar parts throughout the drawings. The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered to be within the scope of the claimed invention.

DETAILED DESCRIPTION

While the specification concludes with claims defining the features of the invention that are regarded as novel, it is believed that the invention will be better understood from a consideration of the description of exemplary embodiments in conjunction with drawings. It is of course to be understood that the embodiments described herein are merely exemplary of the invention, which can be embodied in various forms. Therefore, specific structural and functional details disclosed in relation to the exemplary embodiments described herein are not to be interpreted as limiting, but merely as a representative basis for teaching one skilled in the art to variously employ the present invention in virtually any appropriate form, and it will be apparent to those skilled in the art that the present invention may be practiced without these specific details. Further, the terms and phrases used herein are not intended to be limiting but rather to provide an understandable description of the invention.

As will be explained in greater detail below, exemplary embodiments of the present invention may be implemented to provide a mechanism for classifying and predicting risk of sudden cardiac death (SCD) for a subject using a set of continuous surface electrocardiogram (frequently referred to as "EKG" or "ECG") data recorded for the subject using a cardiac monitor that is specifically configured for this purpose. More specifically, example embodiments can be implemented to provide a mechanism for processing continuously-recorded surface EKG signal data for a subject to extract the features of cardiac repolarization phase curves from the signal and to categorize the extracted cardiac repolarization curves to facilitate detection of occurrences of instability in the cardiac action potential (AP) repolarization phase for the subject. Exemplary embodiments can be implemented to allow for an accurate, easy to perform, and dependable computer-aided evaluation of EKG signal data for determining a risk classification for occurrences of ventricular tachycardia (VT) and ventricular fibrillation (VF) that may lead to SCD for a subject to be made based on a detection of cardiac repolarization instability for the subject. Exemplary embodiments can thereby be implemented to provide a comprehensive, non-invasive, easily repeatable, and cost-effective approach to the evaluation of patients prone to SCD.

Referring now to FIG. 1, an exemplary embodiment of a process 100 for evaluating a risk of SCD for a subject in accordance with the present invention is illustrated. In exemplary process 100, at block 110, a surface EKG signal is recorded for the subject over a predetermined period of time. In exemplary embodiments, as discussed in greater detail below, the EKG signal can be can detected at the body surface and recorded using a monitoring and analysis system that includes a specialized, noninvasive cardiac monitoring device, which may be specifically configured to be capable of using a sampling frequency of at least 1000 Hz for interpreting and recording continuous electrical activity of the heart over an extended period of time (for example, up to 24 or 48 hours) as detected by electrodes attached to the surface of the skin. For example, such a specialized cardiac monitoring device can be used at block 110 for continuously monitoring and logging electrical activity of the heart, as well as other related data from the patient, over the predetermined time period.

In the various examples discussed herein with reference to the drawings, a three-lead EKG was recorded for a subject continuously over a predetermined time period of 24 hours or more. The use of monitoring data acquired over a length of 24 hours or more can yield a set of quality information that is suitable for observing differences in heart function during periods of rest and activity, as the data that is acquired is recorded while patients carry out their usual daily activities. In other words, by recording EKG data from various hours in a day, it is possible to produce a more comprehensive observation of the electrical activity of the heart for a subject, particularly for the purpose of detecting cardiac repolarization stability over time, as such data can be used to detect abnormal electrical activity that may occur randomly or only under certain circumstances.

As with the action potential for cells in other systems of the body, the cardiac action potential is a short-lasting event in which the difference of potential between the interior and the exterior of each cardiac cell rises and falls following a consistent trajectory. Due to the different electrical characteristics of different portions of the heart that result from differentiation of the action potentials, an EKG device, through detection of the electrical impulses generated by depolarization and repolarization of cardiac tissue, is able to record and provide a display indicating the electrical activity of the myocardium (that is, the muscular tissue) of the heart over time as a waveform.

Figure 2:
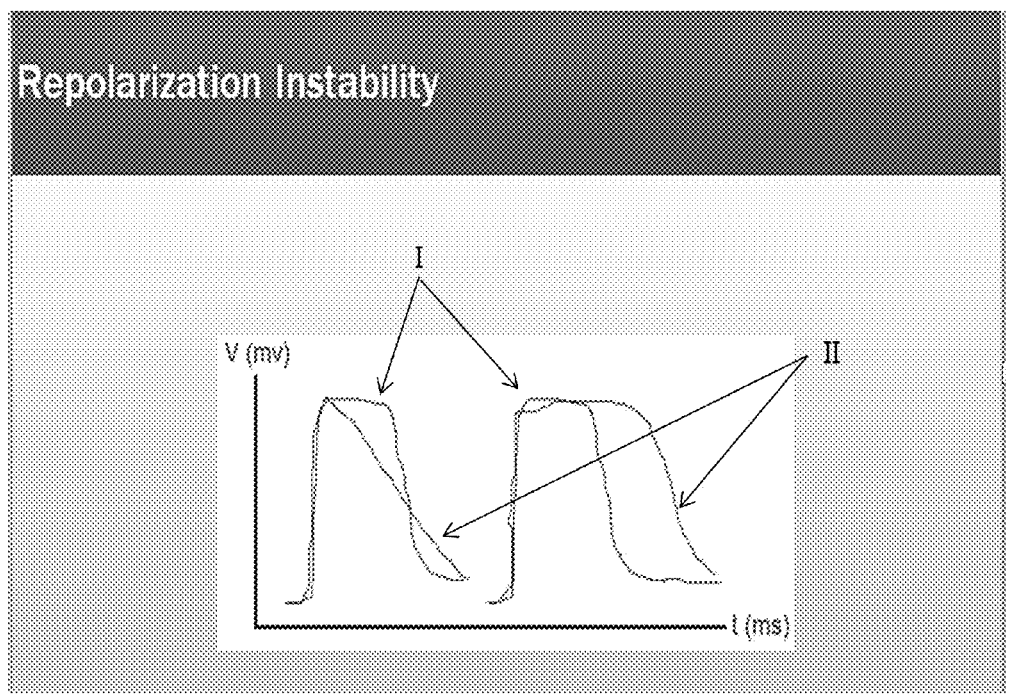
FIG. 2 is a graph illustrating an example of instability observed in the cardiac action potential repolarization phase.
Figure 3A:
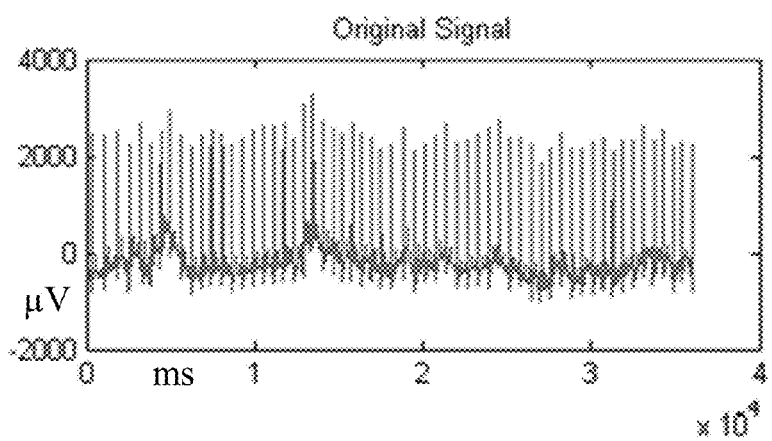
FIGS. 3A-3F are a set of graphs illustrating a process of performing wavelet decomposition and applying a denoising filter to an EKG signal.
Figure 3B:
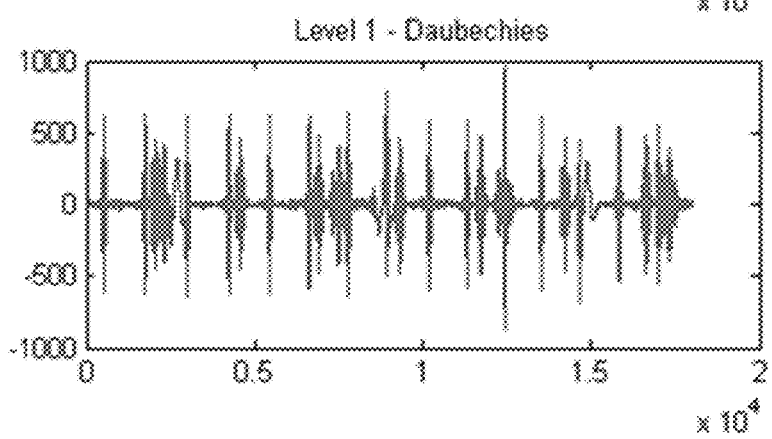
Figure 3C:
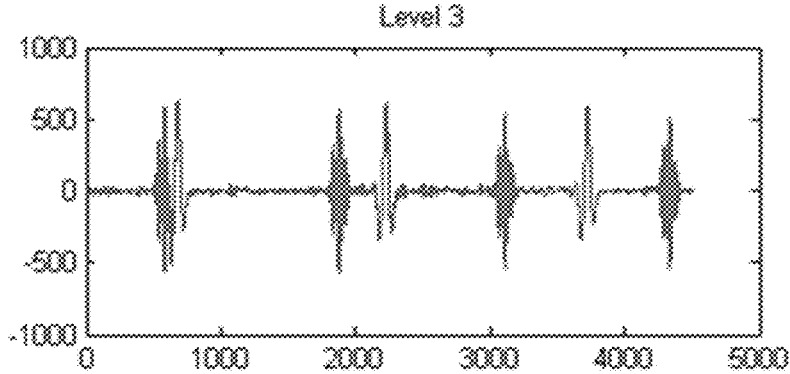
Figure 3D:
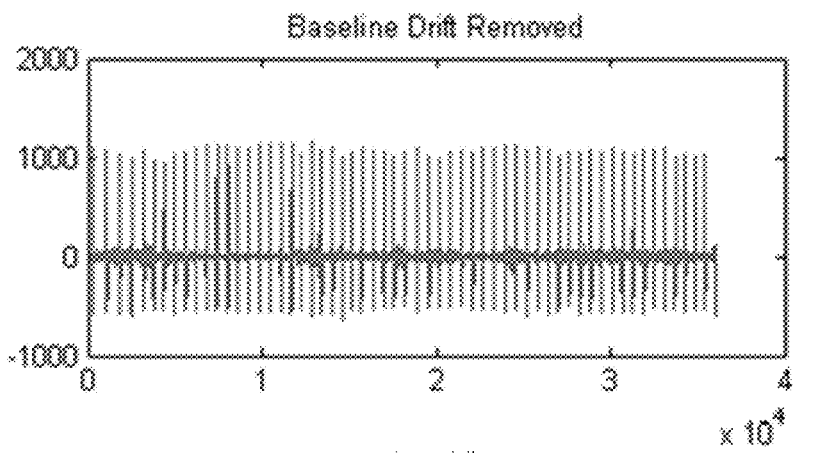
Figure 3E:
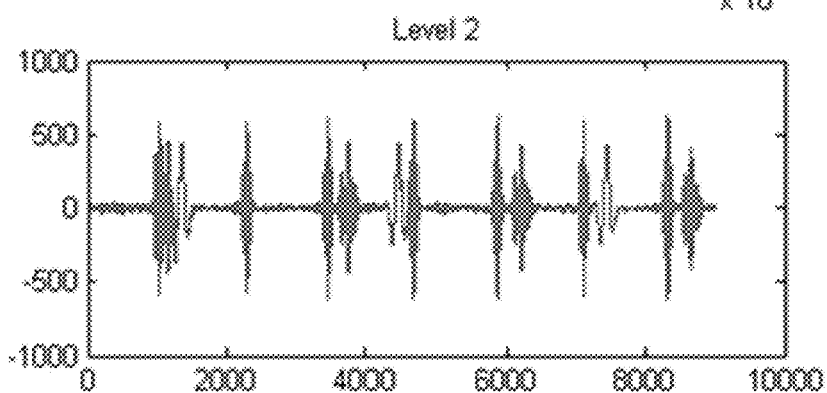
Figure 3F:
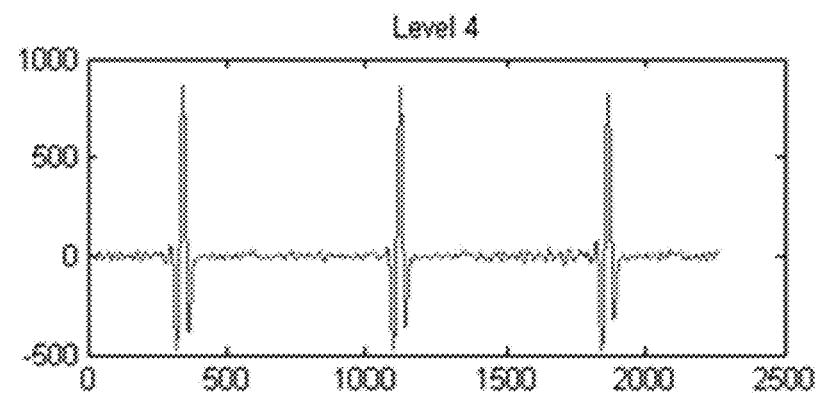

A general example of instability observed in the cardiac action potential repolarization phase is illustrated in FIG. 2. More specifically, in FIG. 2, the curves labeled with (I) in FIG. 2 show the myocardial fiber action potential, and the curves labeled with (II) in FIG. 2 show the myocardial fiber action potential with instability as indicated by triangulation and prolongation of the curves. Research involving invasive or experimental study of cardiac action potential has indicated that AP instability over time in a subject, rather than AP duration, is a hallmark of malignant arrhythmias (see Hondeghem, L. M. et al, Instability and Triangulation of the Action Potential to Predict Serious Proarrhythmia, *Circulation,* 2001; 103:2004-13; Smith J M, Clancy E A, Valeri C R, Ruskin J N, Cohen R J, Electrical alternans and cardiac electrical instability, *Circulation* 1988; 77:110-21).

Nevertheless, the data from a continuous signal over a 24-hour period from a 3-lead EKG may be highly burdensome to process and interpret manually or semi-manually due to the significant amount of data generated. To address this concern, as explained in greater detail below, exemplary process 100 can be performed to implement a series of data processing and analysis operations to extract features from the EKG signal that may then be used to detect cardiac repolarization instability.

More specifically, at block 120, the EKG signal recorded at block 110 is first processed to reduce the amount of noise in the signal. If the leads are worn by the subject for 24 hours, for instance, the level of noise that occurs in the data is significant. Typical examples of noise sources which are commonly known to corrupt EKG signals include, for example, power line interference, electrode contact noise motion artifacts, muscle contraction (electrode myographic, EMG), base line drift, and EKG amplitude modulation with respiration, instrumentation noise generated by electronic devices, electrosurgical noise, and other, less significant noise sources. To address to such noise, any suitable method for filtering and reducing the level of noise in the signal while also preserving the actual signal as intact as possible (see Qi Gao, George, Computerised Detection and Classification of Five Cardiac Conditions, Thesis submitted at Auckland University of Technology, 2003) can be utilized at block 120. In exemplary embodiments, the signal processing performed at block 120 can involve an operation of converting the EKG signal into a set of data in a matrix form that is suitable for use in a numerical computing environment such as MATLAB, and then performing wavelet transformation or other decomposition on the waveform data generated from the EKG signal. Any suitable function or functions for transforming or decomposing the EKG signal such as, for example, Fourier, biorthogonal, or Daubechies wavelet transforms, as well as additional smoothing, denoising, and/or data compression operations, may be implemented at block 120.

In the example illustrated in FIG. 3, the Daubechies wavelet transform, which is commonly used for solving a broad range of signal processing applications, is depicted as being used to perform wavelet decomposition of an original EKG signal. More specifically, beginning with a sample of approximately ⅛th of the signals per hour of EKG lead data, four levels of Daubechies wavelet decomposition are shown in FIG. 3 as being applied to the mother wavelet to produce a cleaner signal. As indicated by the sample reduction per level in FIG. 3, this resulting signal includes fewer samples than the original EKG signal due to down sampling. The original sample size of 40,000 signal points in the current example is reduced to 2,500 following application of the four levels of digital filtering. The resulting signal is then smoothed to remove baseline drift, which is a phenomenon inherent to all EKGs. For this purpose, in the current example, the default "smooth" MATLAB function, which is the moving average filter is used with a frequency of 1000 Hz and period of ¹⁄₁₀₀₀ to perform smoothing on the signal. Finally, to denoise the EKG signal data in the current example, the Savitsky-Golay filter, which is a generalized moving average filter that helps to preserve the peaks and valleys of an EKG signal better than a standard FIR filter (see Kaur, M., Singh, B. & Seema, Comparisons of Different Approaches for Removal of Baseline Wander from ECG Signal, 2nd International Conference and Workshop on Emerging Trends in Technology, *Proceedings of International Journal of Computer Applications,* 2011), is applied to resultant wavelet transform.

Figure 4:
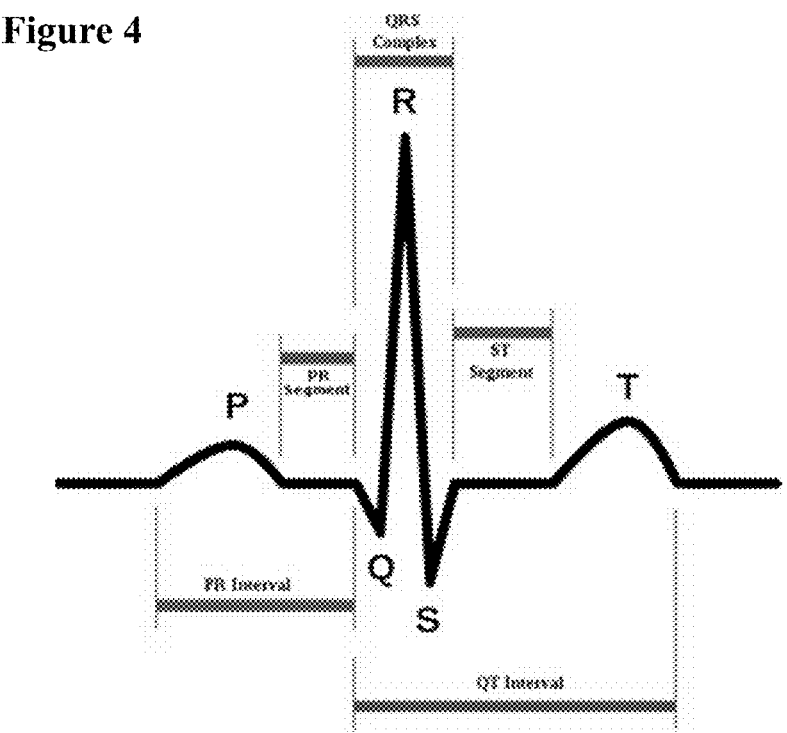
FIG. 4 is a schematic representation of a typical EKG cardiac cycle.

Referring again to FIG. 1, at block 130 of exemplary process 100, after the EKG signal is processed at block 120, the features of the cardiac repolarization curves are automatically extracted from the resulting filtered and denoised wavelet transform obtained from the EKG signal. In particular, as explained in greater detail below, particular aspects of the EKG tracing are utilized to extract the cardiac repolarization curves. A schematic representation of a typical EKG cardiac cycle is provided in FIG. 4. As illustrated in FIG. 4, the typical EKG tracing of the cardiac cycle, which depicts the series of electrical impulses that are produced by particular myocardial cells, consists of a P wave, a QRS complex, a T wave, and a U wave. The baseline of the electrocardiogram (the flat horizontal segments) is measured as the portion of the tracing following the T wave and preceding the next P wave and the segment between the P wave and the following QRS complex.

In the present exemplary embodiment, the first step in extracting the cardiac repolarization curves of each sequential cardiac cycle length in the processed signal at block 130 is to detect the J-points and the peaks of the R waves in each cardiac cycle length. To identify the R peaks in the down sampled signal, values of the signal which are greater than 90% of the maximum value of the actual signal are considered, as these are, invariably, the R peaks. Upon locating the R peaks, the processed signal is then divided into its component RR intervals, which are measurements of the cardiac cycle length in milliseconds. The RR intervals, which are the intervals between an R wave and the next sequential R wave, include the repolarization phase curves. A schematic representation of an example RR interval included within such a processed signal is provided in FIG. 5.

Figure 5:
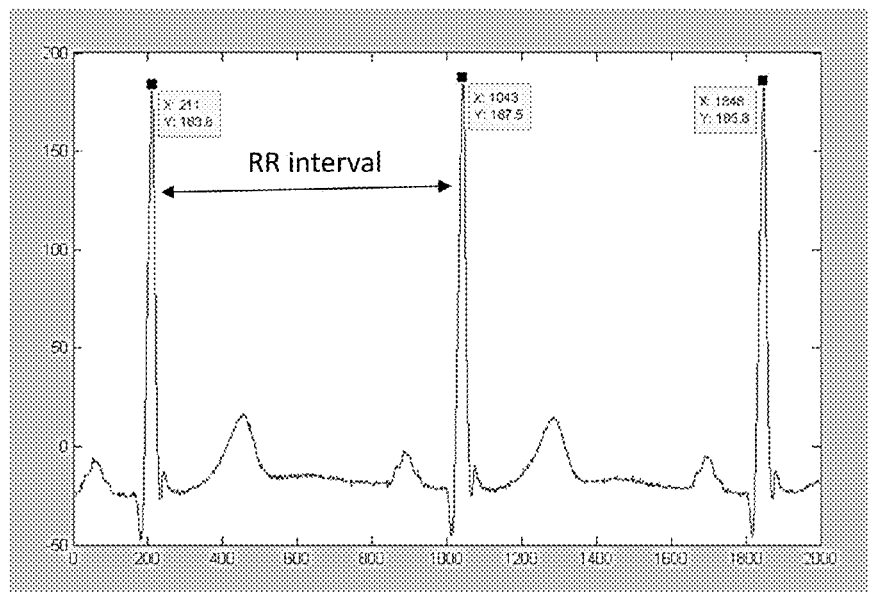
FIG. 5 is schematic representation illustrating an RR interval included within an example EKG signal processed in accordance with an exemplary embodiment of the present invention.

In the present exemplary embodiment, at block 140, after the R peaks and the corresponding RR intervals have been identified in the processed signal, for each pair of consecutive R peaks located at block 130, the distance between the pair of R peaks (for instance, the distance of the example RR interval extracted at block 130 as indicated in FIG. 5) is automatically calculated. For each subject, the lengths of the RR intervals (or cycle lengths) in an EKG signal recorded over 24 hours fall within a range from 500 ms to 1200 ms distributed in a Gaussian form, with the majority of the cycle lengths being between 700 ms and 900 ms.

These calculated distances of the RR intervals from the processed EKG signal data are then utilized as the main parameter for categorization of the extracted repolarization curves in exemplary process 100. More specifically, at block 150, the repolarization curve sections extracted from the EKG signal data (that is, the component RR intervals) are divided into groups according to RR interval length. For example, beginning with an RR interval length range of 500-550 ms as a first group, the extracted repolarization curves may be categorized according to cycle length into groups corresponding to 50 ms RR interval length ranges up to an RR interval length range of 1150-1200 ms as a final group. Of course, it should be noted that the cycle length ranges used to group the extracted repolarization curves is clearly not limited to any specific set of range lengths in exemplary embodiments of the present invention. For instance, as one alternative example, beginning with RR interval lengths falling within range of 300-400 ms as a first group, the extracted repolarization curves may be categorized according to cardiac cycle length into groups corresponding to incremental 100 ms RR interval length ranges (that is, RR interval lengths falling within range of 400-500 ms as a second group, RR interval lengths falling within range of 500-600 ms as a third group, etc.) up to an RR interval length range of 1900-2000 ms as a final group.

In exemplary process 100, at block 160, the extracted repolarization curve sections of each category as grouped at block 150 are automatically plotted and superimposed with one another onto a single graph for that category, and the graph of the superimposed repolarization curves for each category is displayed on a display screen of a display unit via a user interface for physician review. In exemplary embodiments, the J-point that occurs at the end of the QRS complex of each extracted repolarization curve sections is used as a fiducial point in performing superimposition of the extracted repolarization curve sections of each category. In this manner, the J-point, which marks the point at which ventricular depolarization is completed and repolarization begins in the cardiac cycle, can serve as a suitable reference point for superimposing the extracted repolarization curve sections of each category with one another onto a single graph.

Finally, at block 170 of exemplary process 100, an analysis of the resulting superimposition of the repolarization curves for each category to detect instability between the repolarization curves for the subject of the EKG is performed and a prediction of the risk of SCD for the subject is determined based on this analysis. In exemplary embodiments, the analysis for detecting cardiac repolarization instability can be performed qualitatively and/or quantitatively at block 170. More specifically, a qualitative analysis can be performed by a physician or other appropriate medical specialist perform the analysis. A neat set of consistent superimposed repolarization curves in which there is little stagger from the J-point to the beginning of the next P-wave between the superimposed curves will be observed for normal subjects, while a visible level of instability and variation in the superimposed repolarization curves in which the superimposition of the curves occupies a greater portion of the graph will be observed for high-risk subjects. In a quantitative analysis, an automated analysis can be implemented in which, for example, the superimposition of the repolarization curves for each cycle length group is divided into ten segments of equal length, and the amplitude of the total thickness of the superimposed curves is measured in the voltage coordinate direction (for example, in microvolts) for each of the segments. The results of such a quantitative analysis may then be output separately for each cycle length for review by a medical specialist or the automated analysis may be further implemented to determine and output, for example, the maximum voltage obtained for this analysis for each cycle length group or the maximum voltage for the entire set of cycle length groups. In exemplary embodiments, the prediction of the risk of SCD for the subject can be performed based on an evaluation of the detected cardiac repolarization instability in view of an accumulated set of data on a significant number of subjects having profiles of various risk levels for SCD, and this evaluation may, similarly to the analysis for detecting cardiac repolarization instability, be performed qualitatively through observation by a physician or other appropriate medical specialist and/or quantitatively by way of an automated analysis.

Thus, as discussed above, exemplary process 100 can be implemented to provide a mechanism for processing, extracting features from, and categorizing the extracted features of a surface EKG signal for a subject to enable observation of instability in the cardiac repolarization phase for the purpose of predicting a risk of SCD for a subject. As reported by Hondeghem and Leuven (Hondeghem, L. M et al, Instability and Triangulation of the Action Potential to Predict Serious Proarrhythmia, *Circulation,* 2001, 103: 2004-13), myocardial fiber action potential showing repolarization phase triangulation is a strong indicator of development of VT or VF. The surface EKG can be advantageously utilized in exemplary process 100 for superimposing EKG cycle lengths at incremental 100 ms intervals to represent triangulation of the repolarization in a research lab and thereby provide a useful basis for predicting a risk of SCD for the subject.

FIGS. 6A-6F provide illustrations of several examples of graphs of superimposed repolarization curves generated for various subjects using exemplary process 100. As generally illustrated in these examples, certain categories of repolarization phase curve lengths will exhibit a greater degree of instability in the cardiac repolarization phase for subjects with conditions having a higher susceptibility to occurrences of VT and VF as compared with healthy subjects. For example, as indicated in the example provided in FIGS. 6A and 6B for a 59-year old male subject with VT, a moderate amount of instability is observable in the cardiac action repolarization phase for repolarization phase curves detected for the subject with cycle lengths between 900 and 1000 milliseconds is observable, and a greater amount instability is observable for repolarization phase curves detected for the subject with shorter cycle lengths between 500 and 600 milliseconds. Likewise, as indicated in the example provided in FIGS. 6C and 6D for a 12-year old male subject with catechoaminergic VT, a moderate amount instability in the cardiac action repolarization phase for repolarization phase curves detected for the subject with cycle lengths between 900 and 1000 milliseconds is observable, and a greater amount instability is observable for repolarization phase curves detected for the subject with shorter cycle lengths between 600 and 700 milliseconds. In contrast, as indicated in the example provided in FIG. 6E for a 56-year old male subject with ischemic heart disease, there is very little observable instability in the cardiac action repolarization phase for repolarization phase curves detected for the subject with cycle lengths between 900 and 1000 milliseconds. Finally, as indicated in the example provided in FIG. 6F for a 14-year old male subject with familial hypertrophic cardiomyopathy, which is generally associated with a high-risk of sudden cardiac death, there is a significant amount of observable instability in the cardiac action repolarization phase for repolarization phase curves detected for the subject with cycle lengths between 900 and 1000 milliseconds.

Accordingly, the degree of instability in the cardiac action potential repolarization phase that is observable or otherwise detectable in the superimpositions of the repolarization curves that are generated using exemplary process 100 for a subject can be evaluated by a physician or other medical specialist in making a determination of the risk of SCD for the subject. Based on the risk of SCD that is determined for a patient, the physician may then, for instance, make a further determination of whether the use of an ICD would be an appropriate step in treatment of the patient.

As noted above, in exemplary process 100, a specialized cardiac monitoring system can be used at block 110 for continuously monitoring and logging electrical activity of the heart for the recording time period. A general cardiac monitoring device such as a Holter machine is a portable EKG device that can be used for continuously monitoring electrical activity of the heart or cardiac system over an extended time period (typically at least 24 hours) using electrocardiography via a series of electrodes attached to the chest of the subject and recording the electrical heart activity into a data file on a digital memory such as a flash memory device incorporated with the device. In exemplary embodiments of the present invention, a dedicated cardiac monitoring system can be specifically configured with suitably-programmed software and/or hardware components for implementing an integrated set of various aspects of the automatic processing and analysis of the recorded EKG signal data that is performed at blocks 120-170 of exemplary process 100.

In other words, such a special-purpose cardiac monitoring system can be implemented in exemplary embodiments to perform conversion and processing of the EKG signal recorded over the predetermined time period to reduce the amount of noise in the signal (via suitable wavelet decomposition or transform, smoothing, denoising, and/or data compression operations), extraction of the cardiac repolarization curves from the resulting filtered and denoised wavelet transform obtained from the EKG signal data by identifying the R peaks and the corresponding RR intervals in the processed signal data, calculating the distance between each pair of identified consecutive R peaks, dividing the extracted repolarization curves into groups according to RR interval length, superimposing the extracted repolarization curve sections of each grouped category with one another onto a single graph for that category, performing a quantitative analysis of the resulting superimposition of the repolarization curves for each category to detect instability between the repolarization curves for the subject, and displaying the graph of the superimposed repolarization curves for each category and/or a report of the results of the quantitative analysis of the superimposed repolarization curves on a display screen of a display unit incorporated with or attached to the specialized cardiac monitoring system via a user interface implemented by the cardiac monitoring system. The cardiac monitoring system can be implemented to present this information on the display unit using, for instance, a combination of graphical elements and summary tables that are accessible via the user interface.

Figure 7:
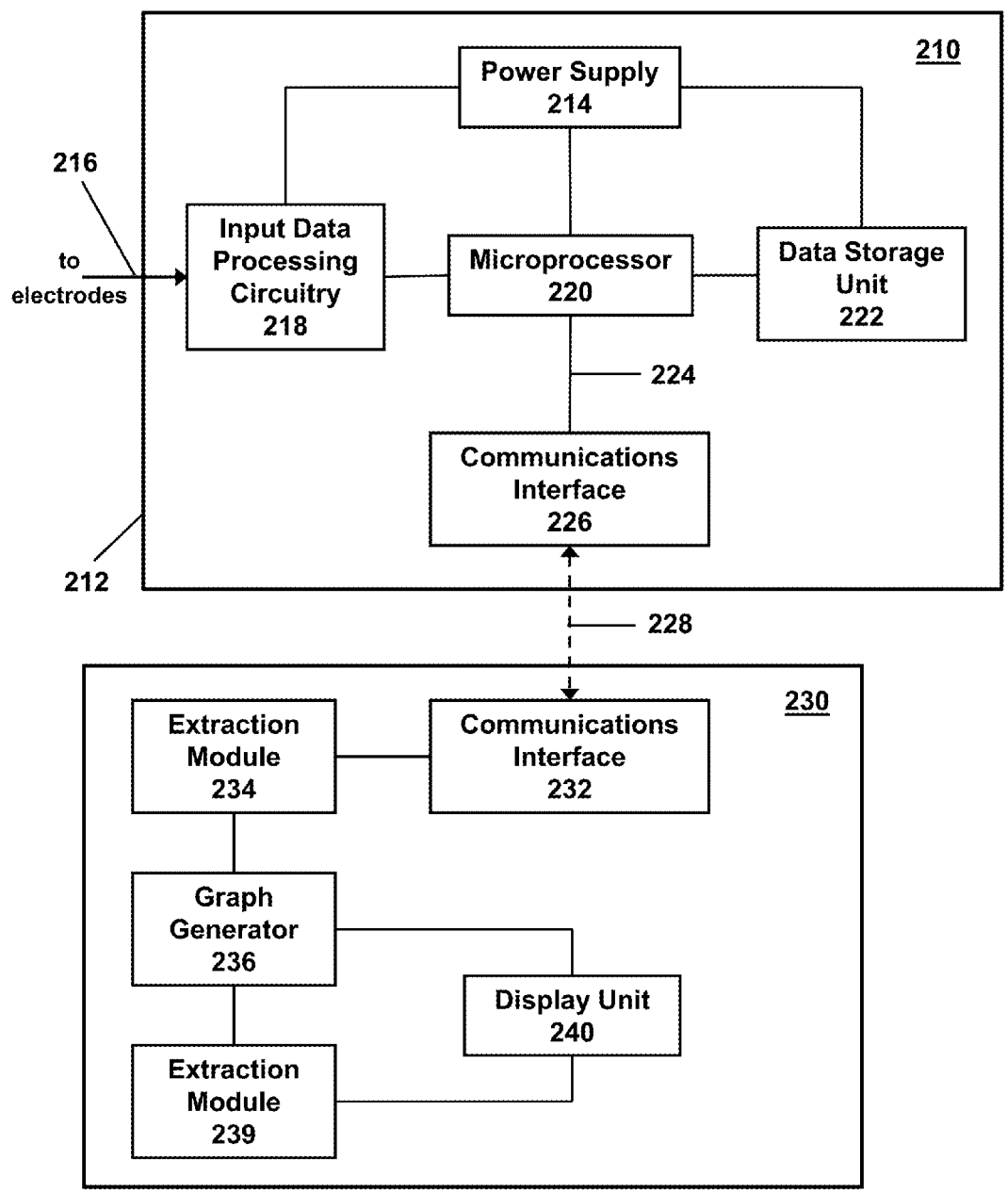
FIG. 7 is a schematic diagram illustrating an exemplary embodiment of a cardiac monitoring and evaluation system implemented in accordance with an exemplary embodiment of the present invention.

Referring now to FIG. 7, a schematic diagram illustrating an exemplary embodiment of a cardiac monitoring and evaluation system 200 in accordance with the present invention is provided. As illustrated in FIG. 7, exemplary system 200 generally includes a monitoring device 210 and an analysis device 230 that are communicatively coupled via a communication link 228. In the present exemplary embodiment, monitoring device 210 is a portable electrocardiograph device (for example, a three-lead EKG) that is wearable by a subject for measuring and recording continuous electrical activity of the subject's heart over an extended monitoring and acquisition time period (for example, up to 24 or 48 hours), as detected by an operably coupled set of electrodes having proximal ends that are directly attached to the subject for detecting cardiac electrical activity, at a high-performance time resolution that suitable to allow for precise identification of the peak positions and shapes of the R waves within the electrocardiographic signals detected by the electrodes (for example, using a sampling frequency of at least 1000 Hz). In exemplary embodiments, monitoring device 210 can be small, lightweight, and portable device configured to be carried on a belt or other harness.

In the present exemplary embodiment, monitoring device 210 generally includes a housing 212 and, incorporated within the housing, a power supply 214 (such as, for example, a battery), input data processing circuitry 218, a microprocessor 220, a data storage unit 222, and a communication interface 226. Power supply 214, which can incorporate, for example, long-life or rechargeable batteries, is provided for powering monitoring device 210. For instance, power supply can be configured to supply power to all electronic components within monitoring device 210 via a power bus. Input data processing circuitry 218 is coupled to distal ends 216 of the electrodes for receiving continuous analog electrocardiographic signals detected by electrodes (for example, a three-lead surface EKG signal) over the monitoring time period and can be configured to perform pre-amplification of the received analog electrocardiographic signals. Input data processing circuitry 218 is coupled to microprocessor 220 at an output end so that the amplified analog electrocardiographic signal at the output of the input data processing circuitry is transmitted to the microprocessor.

Microprocessor 220 is configured with suitable software, hardware, and/or firmware for controlling functions of monitoring device 210 and is coupled to communication interface 226 via a data bus 224. Microprocessor 220 is further coupled to data storage unit 222, which is used by the microprocessor for storing data collected by input data processing circuitry 218 and processed by the microprocessor. In exemplary embodiments, data storage unit 222 can also be used for storing software programs executed by the microprocessor. In alternative exemplary embodiments, software programs running on microprocessor 220 may be stored in a different memory component (not shown) that is distinct from data storage unit 222 or in a memory component integrated with the microprocessor 408 on the same electronic chip.

In the present exemplary embodiments, microprocessor is configured to perform analog-to-digital conversion of the analog electrocardiographic signal from the output of input data processing circuitry 218 to a digital electrocardiographic signal and to perform additional data processing on the digital electrocardiographic signal. More specifically, microprocessor 220 is configured to perform A/D conversion and processing of the EKG signal recorded over the monitoring time period to reduce the amount of noise in the signal and save memory space within data storage device 222 that would otherwise be used for storing all digitized EKG data while also preserving the actual signal as intact as possible (by implementing any suitable functions for performing wavelet decomposition or transform, smoothing, denoising, and/or data compression operations). In exemplary embodiments, microprocessor 220 can also include an internal clock that provides a time-keeping function that allows the digital electrocardiographic signal to be suitably time-stamped when stored in data storage unit 222.

As noted above, microprocessor 220 is configured to store data collected and/or generated by monitoring device 210 in data storage unit 222, which may comprise, for example, a non-volatile memory component such as a flash memory to allow data representing cardiac activity over an extended period of time to be stored or buffered as necessary. Microprocessor 220 is further configured to access communications interface 226 via data bus 224 to communicate with other devices or modules external to monitoring device 210.

For instance, in the present exemplary embodiment, microprocessor 220 is configured to allow for data stored in data storage unit 222 to be transferred to analysis device 230 via communications interface 226. While data storage unit 222 is provided an internal storage component of monitoring device 210 in the present exemplary embodiment, data storage unit 222 may alternatively be provided as an external memory device that is communicatively coupled with microprocessor 220 via communications interface 226.

In exemplary embodiments, the electronic components used in monitoring device 210 may comprise off-the-shelf components or application-specific integrated circuits or other custom-made electronics. In exemplary embodiments, microprocessor 220 of monitoring device 210 may comprise a high-integration component that incorporates, for instance, an analog-to-digital converter along with memory and data interface components of monitoring 210. In exemplary embodiments, monitoring device 210 may also further comprise additional hardware and/or software components that are commonly used for associated or similar types of devices and systems as well as other coupled electronic components not shown in FIG. 7, such as LCD display, buttons, LED, and the like. Microprocessor 220 and other electronic components of monitoring device 210 may be selected to have low power consumption that enables the monitoring device to operate continuously for extended periods of time on a limited power source.

In the present exemplary embodiment, as illustrated in FIG. 7, analysis device 230 generally includes a communications interface 232, a cardiac repolarization curves extraction module 234, a graph generator 236, a sudden cardiac death (SCD) risk evaluation module 238, and a display unit 240. In general, analysis device 230 is configured to perform an analysis of cardiac action potential repolarization phase instability as an indicator for predicting risk of sudden cardiac death for a subject through classification and evaluation of cardiac repolarization curves extracted from the surface EKG data recorded and processed by monitoring device 210. In exemplary embodiments, analysis device 230 can comprise any of a wide range of suitable computing devices such as one or more workstations, desktop computers, laptops, or other personal computers (PCs) (for example, IBM or compatible PC workstations running the MICROSOFT WINDOWS operating system or LINUX OS, MACINTOSH computers running the MAC OSX operating system, or equivalent), non-traditional-computer digital devices such as Personal Digital Assistants (PDAs) and other handheld or portable electronic devices, smart phones, tablet PCs, game consoles, home theater PCs, desktop replacement computers, and the like, or any other suitable information processing devices.

In the present exemplary embodiment, analysis device 230 is communicatively coupled to monitoring device 210 and configured to receive the filtered and denoised wavelet transform obtained from the surface EKG signal by the monitoring device and stored in data storage unit 222 via communications link 228 between communications interface 226 and communications interface 232. In exemplary embodiments, communications link 228 can comprise any suitable wired technology (including optical fiber), wireless technology, or any suitable combination thereof.

Upon receiving the processed surface EKG signal data from monitoring device 210, communications interface 232 transmits the received data to extraction module 234, which is configured to identify and extract a plurality of cardiac repolarization phase curves from the EKG signal. More specifically, in the present exemplary embodiment, extraction module 234 is configured detect the J-points and the peaks of the R waves in each cardiac cycle length in the EKG signal. For this purpose, extraction module 234 can be configured to utilize any suitable recognition function or functions to identify the J-points and the R wave peaks. Extraction module 234 is further configured to, upon locating the R peaks, perform a high-precision identification of the RR intervals within the EKG signal to divide the processed signal into component RR intervals, which are, as discussed above, measurements of the cardiac cycle length in milliseconds.

In the present exemplary embodiment, graph generator 236 is configured to receive the repolarization curve sections extracted from the EKG signal data (that is, the component RR intervals) by extraction module 234 and assign each of the extracted cardiac repolarization phase curves into one of a plurality of groups based on a length of the cardiac repolarization phase curve (that is, according to RR interval length). In particular, for each pair of consecutive R peaks located, graph generator 236 automatically calculates the distance between the pair of R peaks (for instance, the distance of the example RR interval indicated in FIG. 5) and assign each of the extracted repolarization curves to a corresponding group of a plurality of repolarization curve groups that are each defined according to a respective a cycle length range.

Graph generator 236 is further configured to, upon assigning the extracted repolarization curves to the corresponding groups, generate a respective graphical representation for each of the plurality of groups in which the cardiac repolarization phase curves assigned to the group are superimposed with one another in the respective graphical representation for the group. More specifically, the extracted repolarization curve sections of each repolarization curve group are automatically plotted and superimposed with one another onto a single graph for that group. For example, graph generator 236 can be configured to utilize the J-point that occurs at the end of the QRS complex of each extracted repolarization curve section, as recognized by extraction module 234, as a fiducial point in implementing the superimposition of the extracted repolarization curve sections of each group.

In exemplary embodiments, graph generator 236 may also be further configured to generate a display of the graph of the superimposed repolarization curves for each group and output the generated display for each group to display unit 240 for rendering on a display screen of the display unit to provide for review and evaluation via a user interface implemented by analysis device 230 by a physician or other appropriate medical specialist. In particular, via such a display, a specialist will be able to perform a qualitative evaluation of the graph of the superimposed repolarization curves for each group to identify instability between the repolarization curves for any of the groups and assess a risk of sudden cardiac death for the subject of the EKG based on a classification of cardiac repolarization instability as indicated by any of the graphical representations. In general, as discussed above, a set of consistent superimposed repolarization curves in which there is little stagger from the J-point to the beginning of the next P-wave between the superimposed curves will be observed in such a qualitative analysis for normal subjects, while a visible level of instability and variation in the superimposed repolarization curves in which the superimposition of the curves occupies a greater portion of the graph will be observed in one of more of the graphical representations for high-risk subjects.

In the present exemplary embodiment, analysis device 230 further includes risk evaluation module 238 for performing a quantitative analysis of the resulting superimposition of the repolarization curves for each group. More particularly, risk evaluation module 238 is configured to perform an automatic evaluation of the graphical representations generated for the plurality of groups to detect instability between the repolarization curves for any of the groups and determine a risk of sudden cardiac death for the subject of the EKG based on a classification of cardiac repolarization instability as indicated by any of the graphical representations. For example, to perform such an automated quantitative analysis of the superimpositions of the repolarization curves generated by graph generator 236, risk evaluation module 238 can be implemented to perform an analysis by dividing the superimposition of the repolarization curves for each cycle length group into ten segments of equal length and measuring the amplitude of the total thickness of the superimposed curves in the voltage coordinate direction for each of the segments. In exemplary embodiments, risk evaluation module 238 can be configured to generate a separate display or report of the results of such a quantitative analysis for each cycle length and output the generated display for each cycle length to display unit 240 for rendering on the display screen of the display unit to provide for review and evaluation via a user interface implemented by analysis device 230 by a physician or other appropriate medical specialist. Alternatively, or in conjunction therewith, risk evaluation module 238 can be further configured to determine and output, for example, the maximum voltage obtained for this analysis for each cycle length group or the maximum voltage for the entire set of cycle length groups.

In exemplary embodiments, as noted above, the prediction of the risk of SCD for the subject can be performed based on an evaluation of the detected cardiac repolarization instability in view of an accumulated set of data on a significant number of subjects having profiles of various risk levels for SCD, and this evaluation may, similarly to the analysis for detecting cardiac repolarization instability, be performed qualitatively through observation by a physician or other appropriate medical specialist and/or quantitatively by way of an automated analysis implemented by analysis device 230.

In general, it should of course be further noted and understood that FIG. 7 is intended as an example, not as an architectural limitation for different embodiments of the present invention, and therefore, the particular elements depicted in FIG. 7 should not be considered limiting with regard to the various implementations with which exemplary embodiments of the present invention may be provided. For example, while cardiac monitoring and evaluation system 200 is described as having certain functionalities implemented by monitoring device 210 and other functionalities implemented by analysis device 230, the monitoring device may instead by implemented to perform one or more of the functionalities described as being performed by the analysis device (such as, for example, operations described as being performed by extraction module 234) in alternative exemplary embodiments. Likewise, analysis device 230 may instead by implemented to perform one or more of the functionalities described as being performed by monitoring device 230 (such as, for example, signal processing operations or data storage operations described as being performed by microprocessor 220 and data storage device 222) in alternative exemplary embodiments. As another example, the various components and/or storage units of system 200 may all be integrated within the same computing system (for example, monitoring device 210 can be further configured to include a display unit and utilize customized software and/or hardware configured to run embedded software to perform the functionalities that are described in conjunction with the exemplary embodiment illustrated in FIG. 7 as being implemented by analysis device 230.

In further exemplary embodiments, such a specialized cardiac monitoring system may also be configured to perform additional operations for extracting other indices of vulnerability to the development of VF and VT obtained at various heart rates such as, for example, QRS duration, QT interval, corrected QT interval, QT dispersion, T alternans, and high frequency low amplitude after depolarization (HFLA or SAEKG), as well as any other suitable measurements that may be useful for predicting risk of SCD, and to display the results of these additional operations to provide further information that may be useful for the physician for assessing vulnerability to the development of VF and VT and predicting a risk of SCD. Such exemplary embodiments can thereby be implemented to provide health-care institutions the further benefit of avoiding the need to invest in several separate and costly machines such as Signal Average EKG and T-alternans machines (which also require the use of an accompanying treadmill) that are typically used in piecemeal fashion to obtain multiple sets of information that are evaluated together in evaluating a subject's vulnerability to sudden cardiac death.

Moreover, in such exemplary embodiments, the prediction of the risk of SCD for a subject can be determined or further refined based on a composite analysis of observations of instability in the cardiac repolarization phase for the subject along with the other extracted indices of vulnerability to the development of VF and VT, as well as other relevant information pertaining to the subject such as medical history, physical examination results, any diagnosed conditions, echo indices, and baroreceptor sensitivity reflex (BRSR). In exemplary embodiments, any of the indices of QRS duration, QT interval, corrected QT interval, QT dispersion, T alternans, SAEKG, as well as echo indices and BRSR, may be calculated based on the data recorded by the cardiac monitoring system over the predetermined monitoring time period. In an example in which such a composite analysis was employed by the inventors for predicting the risk of SCD for a set of 124 patients, this analysis resulted in 72 of the patients being determined to have a low risk of SCD and 52 of the patients being determined to have a high risk of SCD. The positive predictive value for patients with sudden death or ICD shock in this example analysis was 80.7 percent, while the negative predictive value was 100 percent. These sensitivity and specificity measures in the example are far superior to any existing detection methods presently in use, which lack sufficient specificity and produce a significant number of false positives, unnecessarily generating anxiety in healthy subjects and causing expensive physician review and additional treatment (often surgical implanting of an ICD) that may be uncomfortable and potentially dangerous for the subject.

In additional exemplary embodiments, a specialized cardiac monitoring system may also be further configured to perform an initial analysis of the instability in the cardiac repolarization phase indicated by the graphs of the superimposed grouped repolarization curves to identify candidate graphs that may be worthy of further study by the physician so that the physician can quickly pinpoint these areas when analyzing the signal. In various exemplary embodiments, some portions of the processing described herein may be performed by a specialized cardiac monitoring system while other portions may be performed by another computer system that is configured to connect to and receive data uploaded from the cardiac monitoring system.

As explained above, exemplary embodiments of the present invention can be implemented to provide a mechanism for recording and analyzing the EKG signal data for a subject (for example, in a manner that is similar to a Holter study) over an extended period of time for the purpose of detecting cardiac repolarization instability to predict vulnerability of the subject to the development of VF and VT in a manner that is cost-efficient, noninvasive, highly accurate, and convenient for the subject. Such a mechanism provides a novel manner of processing and analyzing electrophysiological data to generate information previously unavailable in standard Holter studies. While there is an abundance of literature available on decomposing EKG mother wavelets and subsequent filtering techniques used in prior Holter studies, no further processing and analysis is performed in the vast majority of these studies. For example, none of these prior studies involve any extraction of features such as cardiac repolarization curves from the EKG signal data being performed.

Moreover, prior analyses have not involved processing and analysis on a continuous EKG signal data obtained over periods of 24 hours or more in length. As noted above, data processing is performed in exemplary embodiments of the present invention to address the fact that the recording of a 24-hour, 3-lead EKG signal produces a significant amount of data that can be prohibitive to store, process, and interpret manually or semi-manually. In developing a mechanism to address this issue via automated EKG signal processing, two primary areas concern for the inventors of the present invention involved automation of the initial processing of the significant amount of recorded EKG signal data and ensuring that the signal processing is performed in a manner that significantly reduces the noise level of the signal without detrimentally impacting the quality of the signal to thereby enhance the quality of the information obtained through processing of the EKG signal data.

Aspects of exemplary embodiments of the present invention described herein can be implemented using one or more program modules and data storage units. As used herein, the term "modules", "program modules", "components", "systems", "tools", "utilities", and the like include routines, programs, objects, components, data structures, and instructions, or instructions sets, and so forth that perform particular tasks or implement particular abstract data types. As can be appreciated, the modules refer to computer-related entities that can be implemented as software, hardware, firmware and/or other suitable components that provide the described functionality, and which may be loaded into memory of a machine embodying or embodied within an exemplary embodiment of the present invention. Aspects of the modules may be written in a variety of programming languages, such as C, C++, Java, etc. The functionality provided by modules used for aspects of exemplary embodiments described herein can be combined and/or further partitioned.

As used herein, the terms "data storage unit," "data store", "storage unit", and the like can refer to any suitable memory device that may be used for storing data, including manual files, machine readable files, and databases. The modules and/or storage units can all be implemented and run on the same computing system (for example, the exemplary computer system illustrated in FIG. 8 and described below) or they can be implemented and run on different computing systems. For example, one or modules can be implemented on a personal computer operated by a user while other modules can be implemented on a remote server and accessed via a network.

In exemplary embodiments, the program modules utilized in exemplary embodiments of the present invention can be configured for incorporation within any suitable computing environment as a plug-in, add-on, or extension. As used herein, the term "plug-in" can refer to a software application or module program, or one or more computer instructions, which may or may not be in communication with other software applications or modules, that interacts with a host application to provide specified functionality, and which may include any file, image, graphic, icon, audio, video, or any other attachment. In other exemplary embodiments, the program modules can be implemented within a standalone program that is run as a separate computer process, a portable application, a native component of an electrocardiogram evaluation or a more general physiologic evaluation tool, a part of a software bundle, or any other suitable implementation.

In the preceding description, for purposes of explanation, numerous specific details are set forth in order to provide a thorough understanding of the described exemplary embodiments. Nevertheless, one skilled in the art will appreciate that many other embodiments may be practiced without these specific details and structural, logical, and electrical changes may be made.

Some portions of the exemplary embodiments described above are presented in terms of algorithms and symbolic representations of operations on data bits within a processor-based system. The operations are those requiring physical manipulations of physical quantities. These quantities may take the form of electrical, magnetic, optical, or other physical signals capable of being stored, transferred, combined, compared, and otherwise manipulated, and are referred to, principally for reasons of common usage, as bits, values, elements, symbols, characters, terms, numbers, or the like. Nevertheless, it should be noted that all of these and similar terms are to be associated with the appropriate physical quantities and are merely convenient labels applied to these quantities. Unless specifically stated otherwise as apparent from the description, terms such as "executing" or "processing" or "computing" or "calculating" or "determining" or the like, may refer to the action and processes of a processor-based system, or similar electronic computing device, that manipulates and transforms data represented as physical quantities within the processor-based system's storage into other data similarly represented or other such information storage, transmission or display devices.

Exemplary embodiments of the present invention can be realized in hardware, software, or a combination of hardware and software. Exemplary embodiments can be realized in a centralized fashion in one computer system or in a distributed fashion where different elements are spread across several interconnected computer systems. Any kind of computer system—or other apparatus adapted for carrying out the methods described herein—is suited. A typical combination of hardware and software could be a general-purpose computer system with a computer program that, when being loaded and executed, controls the computer system such that it carries out the methods described herein.

Exemplary embodiments of the present invention can also be embedded in a computer program product, which comprises all the features enabling the implementation of the methods described herein, and which—when loaded in a computer system—is able to carry out these methods. Computer program means or computer program as used in the present invention indicates any expression, in any language, code or notation, of a set of instructions intended to cause a system having an information processing capability to perform a particular function either directly or after either or both of the following: (a) conversion to another language, code or, notation; and (b) reproduction in a different material form.

A computer system in which exemplary embodiments can be implemented may include, inter alia, one or more computers and at least a computer program product on a computer readable medium, allowing a computer system, to read data, instructions, messages or message packets, and other computer readable information from the computer readable medium. The computer readable medium may include non-volatile memory, such as ROM, Flash memory, Disk drive memory, CD-ROM, and other permanent storage. Additionally, a computer readable medium may include, for example, volatile storage such as RAM, buffers, cache memory, and network circuits. Furthermore, the computer readable medium may comprise computer readable information in a transitory state medium such as a network link and/or a network interface, including a wired network or a wireless network, that allow a computer system to read such computer readable information.

Figure 8:
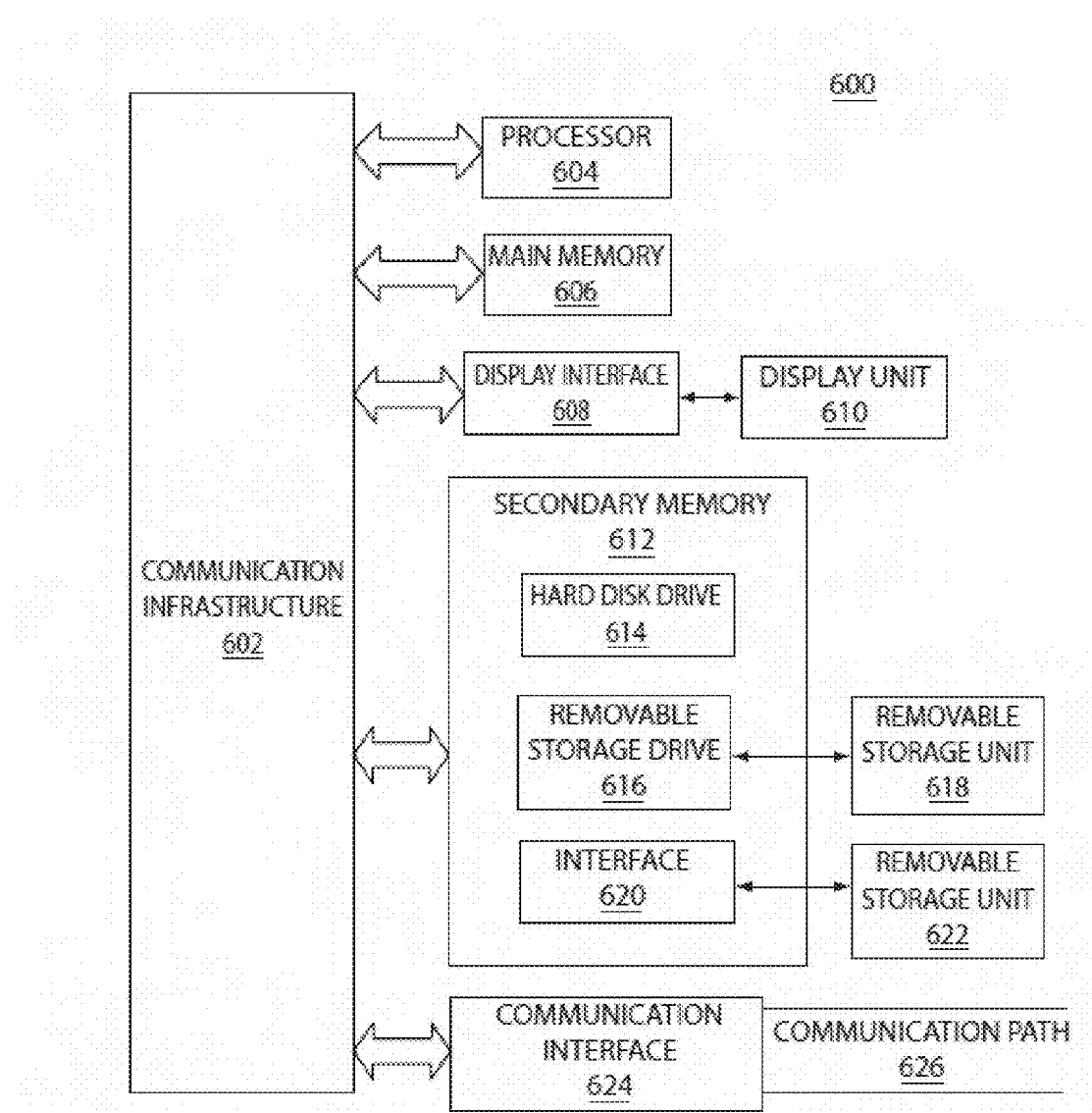
FIG. 8 is a block diagram of an exemplary computer system that can be used for implementing exemplary embodiments of the present invention.

FIG. 8 is a block diagram of an exemplary computer system 600 that can be used for implementing exemplary embodiments of the present invention. Computer system 600 includes one or more processors, such as processor 604. Processor 604 is connected to a communication infrastructure 602 (for example, a communications bus, cross-over bar, or network). Various software embodiments are described in terms of this exemplary computer system. After reading this description, it will become apparent to a person of ordinary skill in the relevant art(s) how to implement the invention using other computer systems and/or computer architectures.

Exemplary computer system 600 can include a display interface 608 that forwards graphics, text, and other data from the communication infrastructure 602 (or from a frame buffer not shown) for display on a display unit 610. Computer system 600 also includes a main memory 606, which can be random access memory (RAM), and may also include a secondary memory 612. Secondary memory 612 may include, for example, a hard disk drive 614 and/or a removable storage drive 616, representing a floppy disk drive, a magnetic tape drive, an optical disk drive, etc. Removable storage drive 616 reads from and/or writes to a removable storage unit 618 in a manner well known to those having ordinary skill in the art. Removable storage unit 618, represents, for example, a floppy disk, magnetic tape, optical disk, etc. which is read by and written to by removable storage drive 616. As will be appreciated, removable storage unit 618 includes a computer usable storage medium having stored therein computer software and/or data.

In exemplary embodiments, secondary memory 612 may include other similar means for allowing computer programs or other instructions to be loaded into the computer system. Such means may include, for example, a removable storage unit 622 and an interface 620. Examples of such may include a program cartridge and cartridge interface (such as that found in video game devices), a removable memory chip (such as an EPROM, or PROM) and associated socket, and other removable storage units 622 and interfaces 620 which allow software and data to be transferred from the removable storage unit 622 to computer system 600.

Computer system 600 may also include a communications interface 624. Communications interface 624 allows software and data to be transferred between the computer system and external devices. Examples of communications interface 624 may include a modem, a network interface (such as an Ethernet card), a communications port, a PCM-CIA slot and card, etc. Software and data transferred via communications interface 624 are in the form of signals which may be, for example, electronic, electromagnetic, optical, or other signals capable of being received by communications interface 624. These signals are provided to communications interface 624 via a communications path (that is, channel) 626. Channel 626 carries signals and may be implemented using wire or cable, fiber optics, a phone line, a cellular phone link, an RF link, and/or other communications channels.

In this document, the terms "computer program medium," "computer usable medium," and "computer readable medium" are used to generally refer to media such as main memory 606 and secondary memory 612, removable storage drive 616, a hard disk installed in hard disk drive 614, and signals. These computer program products are means for providing software to the computer system. The computer readable medium allows the computer system to read data, instructions, messages or message packets, and other computer readable information from the computer readable medium. The computer readable medium, for example, may include non-volatile memory, such as Floppy, ROM, Flash memory, Disk drive memory, CD-ROM, and other permanent storage. It can be used, for example, to transport information, such as data and computer instructions, between computer systems. Furthermore, the computer readable medium may comprise computer readable information in a transitory state medium such as a network link and/or a network interface including a wired network or a wireless network that allow a computer to read such computer readable information.

Computer programs (also called computer control logic) are stored in main memory 606 and/or secondary memory 612. Computer programs may also be received via communications interface 624. Such computer programs, when executed, can enable the computer system to perform the features of exemplary embodiments of the present invention as discussed herein. In particular, the computer programs, when executed, enable processor 604 to perform the features of computer system 600. Accordingly, such computer programs represent controllers of the computer system.

While the invention has been described in detail with reference to exemplary embodiments, it will be understood by those skilled in the art that various changes and alternations may be made and equivalents may be substituted for elements thereof without departing from the scope of the invention as defined by the appended claims. In addition, many modifications may be made to adapt a particular application or material to the teachings of the invention without departing from the essential scope thereof.

Variations described for exemplary embodiments of the present invention can be realized in any combination desirable for each particular application. Thus particular limitations, and/or embodiment enhancements described herein, which may have particular limitations need be implemented in methods, systems, and/or apparatuses including one or more concepts describe with relation to exemplary embodiments of the present invention.

Therefore, it is intended that the invention not be limited to the particular embodiments disclosed herein for carrying out this invention, but that the invention will include all embodiments falling within the scope of the present application as set forth in the following claims, wherein reference to an element in the singular, such as by use of the article "a" or "an" is not intended to mean "one and only one" unless specifically so stated, but rather "one or more." Moreover, no claim element is to be construed under the provisions of 35 U.S.C. §112, sixth paragraph, unless the element is expressly recited using the phrase "means for" or "step for." These following claims should be construed to maintain the proper protection for the present invention.

What is claimed is:

1. A method for predicting risk of sudden cardiac death for a subject through analysis of surface electrocardiographic data recorded for the subject, the method comprising:
processing a continuous surface electrocardiogram (EKG) signal received for the subject over a predetermined period of time to identify and extract a plurality of cardiac repolarization phase curves from the EKG signal in which each extracted cardiac repolarization phase curve represents an interval in the EKG signal extending between a corresponding feature of a respective cardiac cycle embodied in the EKG signal and the corresponding feature of a respective next sequential cardiac cycle embodied in the EKG signal;
assigning each of the extracted cardiac repolarization phase curves into one of a plurality of groups that each corresponds to a respective range of cardiac repolarization phase curve time durations by determining a time duration of the cardiac repolarization phase curve between the corresponding feature of the respective cardiac cycle for the cardiac repolarization phase curve and the corresponding feature of the respective next sequential cardiac cycle and assigning the cardiac repolarization phase curve to the group for which the respective range of time durations includes the time duration of the cardiac repolarization phase curve;
generating a respective graphical representation for each of the plurality of groups in which the cardiac repolarization phase curves assigned to the group are superimposed with one another in the respective graphical representation for the group; and
evaluating the graphical representations generated for the plurality of groups to assess a risk of sudden cardiac death for the subject based on a classification of cardiac repolarization instability indicated by variations in voltage levels between the cardiac repolarization phase curves superimposed within the graphical representations.

2. The method of claim 1, wherein the predetermined period of time is at least 24 hours, and further comprising detecting the EKG signal using a three-lead EKG with a sampling frequency of at least 1000 hertz over the predetermined time period.

3. The method of claim 1, wherein processing the EKG signal comprises performing at least one operation selected from wavelet decomposition or transform, smoothing, denoising, and data compression operations.

4. The method of claim 1, wherein the corresponding feature of each cardiac cycle embodied in the EKG signal is a peak of an R wave, and wherein identification and extraction of the plurality of cardiac repolarization phase curves from the EKG signal comprises detecting a peak of an R wave in each cardiac cycle of the EKG signal and dividing the EKG signal into a plurality of component RR intervals of the EKG signal by extracting each component RR interval of the EKG signal between the peak of the R wave of a respective cardiac cycle embodied in the EKG signal and the peak of the R wave of a respective next sequential cardiac cycle embodied in the EKG signal.

5. The method of claim 4, wherein the respective range of cardiac repolarization phase curve time durations to which each of the plurality of groups corresponds is a respective range of RR interval time durations, and wherein assigning each of the extracted cardiac repolarization phase curves into one of the plurality of groups comprises determining a time duration of each of the component RR intervals and assigning each of the component RR intervals to the group for which the respective range of RR interval time durations includes the time duration of the component RR interval.

6. The method of claim 1, further comprising detecting the J-point of each cardiac repolarization phase curve, and wherein the detected J-points are used as fiducial points to superimpose the cardiac repolarization phase curves assigned to each group with one another in the respective graphical representation for the group.

7. The method of claim 1, wherein evaluating the graphical representations generated for the plurality of groups comprises performing an analysis of a level of cardiac repolarization instability indicated by heterogeneity in voltage levels between the superimposed cardiac repolarization phase curves in the graphical representation for each group.

8. The method of claim 7, further comprising rendering a display of the graphical representations generated for the plurality of groups on a display screen of a display unit via a user interface, and wherein the analysis of the level of cardiac repolarization instability between the superimposed cardiac repolarization phase curves in the graphical representation for each group is a qualitative analysis performed by a specialist accessing the user interface to review the rendered display of the graphical representations.

9. The method of claim 7, wherein the analysis of the level of cardiac repolarization instability between the superimposed cardiac repolarization phase curves in the graphical representation for each group is a quantitative analysis that is automatically performed.

10. The method of claim 9, wherein the automatically performed quantitative analysis comprises dividing the graphical representation generated for each group into a plurality of segments and evaluating an aggregate thickness in the voltage coordinate direction of the superimposed cardiac repolarization phase curves in the graphical representation for each segment.

11. The method of claim 7, wherein the classification of cardiac repolarization instability indicated by the graphical representations is selected from a plurality of classifications including indications of ventricular tachycardia (VT) and indicative of ventricular fibrillation (VF).

12. The method of claim 7, wherein the classification of cardiac repolarization instability indicated by the graphical representations is determined to assess the risk of sudden cardiac death for the subject in view of an accumulated set of prior data from a plurality of subjects having profiles indicative of various risk levels for sudden cardiac death.

13. The method of claim 1, further comprising extracting at least one additional indicator of the risk of sudden cardiac death for the subject from the EKG signal selected from QRS duration, QT interval, corrected QT interval, QT dispersion, T alternans, high frequency low amplitude after depolarization (HFLA or SAEKG), echo indices, and baroreceptor sensitivity reflex, and wherein the risk of sudden cardiac death for the subject is further assessed based on the at least one additional indicator of the risk of sudden cardiac death for the subject extracted from the EKG signal.

14. The method of claim 13, wherein the risk of sudden cardiac death for the subject is further assessed based on at least one type of data recorded for the subject selected from diagnostic data, medical history data, physical examination data, and laboratory study data.

15. A cardiac monitoring and analysis system for predicting risk of sudden cardiac death for a subject through analysis of surface electrocardiographic data recorded for the subject, the system comprising:
a monitoring unit that receives and records a continuous surface electrocardiogram (EKG) signal for the subject over a predetermined period of time;
an extraction module that receives the EKG signal from the monitoring unit and processes the EKG signal to identify and extract a plurality of cardiac repolarization phase curves from the EKG signal in which each extracted cardiac repolarization phase curve represents an interval in the EKG signal extending between a corresponding feature of a respective cardiac cycle embodied in the EKG signal and the corresponding feature of a respective next sequential cardiac cycle embodied in the EKG signal; and
a graph generator module that:
assigns each of the extracted cardiac repolarization phase curves into one of a plurality of groups that each corresponds to a respective range of cardiac repolarization phase curve time durations by determining a time duration of the cardiac repolarization phase curve between the corresponding feature of the respective cardiac cycle for the cardiac repolarization phase curve and the corresponding feature of the respective next sequential cardiac cycle and assigning the cardiac repolarization phase curve to the group for which the respective range of time durations includes the time duration of the cardiac repolarization phase curve, and
generates a respective graphical representation for each of the plurality of groups in which the cardiac repolarization phase curves assigned to the group are superimposed with one another in the respective graphical representation for the group; and
a risk evaluation module that generates an output indicative of cardiac repolarization instability between the cardiac repolarization phase curves superimposed within the graphical representations and renders a display of the output on a display screen of a display unit.

16. The system of claim 15, wherein the monitoring unit comprises a portable, three-lead EKG device with a sampling frequency of at least 1000 hertz that is configured to obtain the EKG signal via an operably coupled set of electrodes having proximal ends that are directly attached to the subject, and wherein the predetermined period of time is at least 24 hours.

17. The system of claim 16, wherein the EKG device comprises a housing having, incorporated therein, a power supply configured to supply power to the EKG device, an input data processing circuit coupled to distal ends of the electrodes and configured to receive and pre-amplify the EKG signal, a data store, and a processor configured to receive the EKG signal from the input data processing circuit, perform signal processing on the EKG signal, and access the data store to store the processed EKG signal therein.

18. The system of claim 17, wherein the processor is configured to perform analog-to-digital conversion of the EKG signal received from the input data processing circuit and to perform at least one operation selected from wavelet decomposition or transform, smoothing, denoising, and data compression operations on the converted EKG signal.

19. The system of claim 17, further comprising an analysis device that is communicatively coupled to the EKG device via a communication link, wherein the processor is configured to access the data store to transmit the processed EKG signal stored therein to the analysis device via the communication link, and wherein the analysis device includes the extraction module, the graph generator module, the risk evaluation module, and the display unit.

20. The system of claim 19, wherein the display of the output that is rendered on the display screen of the display unit by the risk evaluation module is a display of the graphical representations that is accessible via a user interface component of the analysis device.

21. The system of claim 20, wherein the user interface component is configured to be accessed by a specialist to allow for the specialist to perform a qualitative analysis of a level of cardiac repolarization instability indicated by heterogeneity in voltage levels between the superimposed cardiac repolarization phase curves in the graphical representation for each group to assess a risk of sudden cardiac death for the subject based on a classification of the cardiac repolarization instability indicated by variations in voltage levels between the cardiac repolarization phase curves superimposed within the graphical representations.

22. The system of claim 19, wherein the risk evaluation module is configured to automatically perform a quantitative analysis of a level of cardiac repolarization instability indicated by heterogeneity in voltage levels between the superimposed cardiac repolarization phase curves in the graphical representation for each group.

23. The system of claim 22, wherein the output generated by the risk evaluation is a report indicating a measure of the heterogeneity in voltage levels between the superimposed cardiac repolarization phase curves in the graphical representation for each group.

24. The system of claim 23, wherein the risk evaluation module is configured to perform an assessment of a risk of sudden cardiac death for the subject based on a classification of the cardiac repolarization instability indicated by variations in voltage levels between the cardiac repolarization phase curves superimposed within the graphical representations, and wherein the output generated by the risk evaluation is a report indicative of the results of the assessment.

25. The system of claim 15, wherein the corresponding feature of each cardiac cycle embodied in the EKG signal is a peak of an R wave, and wherein the extraction module is configured to identify and extract the plurality of cardiac repolarization phase curves from the EKG signal by detecting a peak of an R wave in each cardiac cycle of the EKG signal and dividing the EKG signal into a plurality of component RR intervals of the EKG signal by extracting each component RR interval of the EKG signal between the peak of the R wave of a respective cardiac cycle embodied in the EKG signal and the peak of the R wave of a respective next sequential cardiac cycle embodied in the EKG signal.

26. The system of claim 25, wherein the respective range of cardiac repolarization phase curve time durations to which each of the plurality of groups corresponds is a respective range of RR interval time durations, and wherein the graph generator is configured to assign each of the extracted cardiac repolarization phase curves into one of the plurality of groups by determining a time duration of each of the component RR intervals and assigning each of the component RR intervals to the group for which the respective range of RR interval time durations includes the time duration of the component RR interval.

27. A computer apparatus, comprising:
a processor, and a memory storing computer readable instructions for execution by the processor to perform a method for predicting risk of sudden cardiac death for a subject through analysis of surface electrocardiographic data recorded for the subject, and wherein the method comprises:
processing a continuous surface electrocardiogram (EKG) signal received for the subject over a predetermined period of time to identify and extract a plurality of cardiac repolarization phase curves from the EKG signal in which each extracted cardiac repolarization phase curve represents an interval in the EKG signal extending between a corresponding feature of a respective cardiac cycle embodied in the EKG signal and the corresponding feature of a respective next sequential cardiac cycle embodied in the EKG signal;
assigning each of the extracted cardiac repolarization phase curves into one of a plurality of groups that each corresponds to a respective range of cardiac repolarization phase curve time durations by determining a time duration of the cardiac repolarization phase curve between the corresponding feature of the respective cardiac cycle for the cardiac repolarization phase curve and the corresponding feature of the respective next sequential cardiac cycle and assigning the cardiac repolarization phase curve to the group for which the respective range of time durations includes the time duration of the cardiac repolarization phase curve; and
generating a respective graphical representation for each of the plurality of groups in which the cardiac repolarization phase curves assigned to the group are superimposed with one another in the respective graphical representation for the group.

* * * * *